(12) United States Patent
Rauls et al.

(10) Patent No.: US 10,294,182 B2
(45) Date of Patent: May 21, 2019

(54) METHOD AND DEVICE FOR SEPARATING A SUBSTANCE OUT OF A SOLUTION

(71) Applicant: BASF SE, Ludwigshafen (DE)

(72) Inventors: Matthias Rauls, Blieskastel (DE); Stefan Ziegler, Eußerthal (DE); Martin Haubner, Eppelheim (DE)

(73) Assignee: BASF SE, Ludwigshafen am Rhein (DE)

( * ) Notice: Subject to any disclaimer, the term of this patent is extended or adjusted under 35 U.S.C. 154(b) by 215 days.

(21) Appl. No.: 15/127,135

(22) PCT Filed: Mar. 13, 2015

(86) PCT No.: PCT/EP2015/055279
§ 371 (c)(1),
(2) Date: Sep. 19, 2016

(87) PCT Pub. No.: WO2015/140062
PCT Pub. Date: Sep. 24, 2015

(65) Prior Publication Data
US 2017/0240494 A1    Aug. 24, 2017

(30) Foreign Application Priority Data

Mar. 19, 2014    (EP) ..................... 14160645

(51) Int. Cl.
*B01D 9/00*    (2006.01)
*C07C 29/56*    (2006.01)
(Continued)

(52) U.S. Cl.
CPC ................ *C07C 37/84* (2013.01); *B01D 3/10* (2013.01); *B01D 9/0031* (2013.01);
(Continued)

(58) Field of Classification Search
CPC ........ B01D 3/10; B01D 11/04; B01D 9/0077; B01D 9/0036; B01D 9/0031; B01D 9/00;
(Continued)

(56) References Cited

U.S. PATENT DOCUMENTS 3,357,196 A * 12/1967 Dutcher ............... B01D 9/0013
62/540
3,739,035 A    6/1973 Webb et al.
(Continued)

FOREIGN PATENT DOCUMENTS

CH     350461 A    11/1960
DE     330225 C    12/1920
(Continued)

OTHER PUBLICATIONS

International Search Report for PCT/EP2015/055279 dated Jun. 18, 2015.

*Primary Examiner* — Joseph W Drodge
(74) *Attorney, Agent, or Firm* — Drinker Biddle & Reath LLP

(57) ABSTRACT

The present invention relates to a method for separating off a substance from a solution, in which electromagnetic radiation is radiated into the solution, an intensity of the electromagnetic radiation which has been scattered by crystals located in the solution is detected, the detected intensity is compared with a desired intensity ($I_S$) and the temperature of the solution is regulated depending on the difference between the detected intensity and the desired intensity ($I_S$) in such a way that the amount of this difference is reduced. If the amount of the difference between the detected intensity and the desired intensity ($I_S$) is less than a limiting value, a crystallization method is started in which crystals of the substance are obtained which are then separated off.

15 Claims, 5 Drawing Sheets

Figure 1:
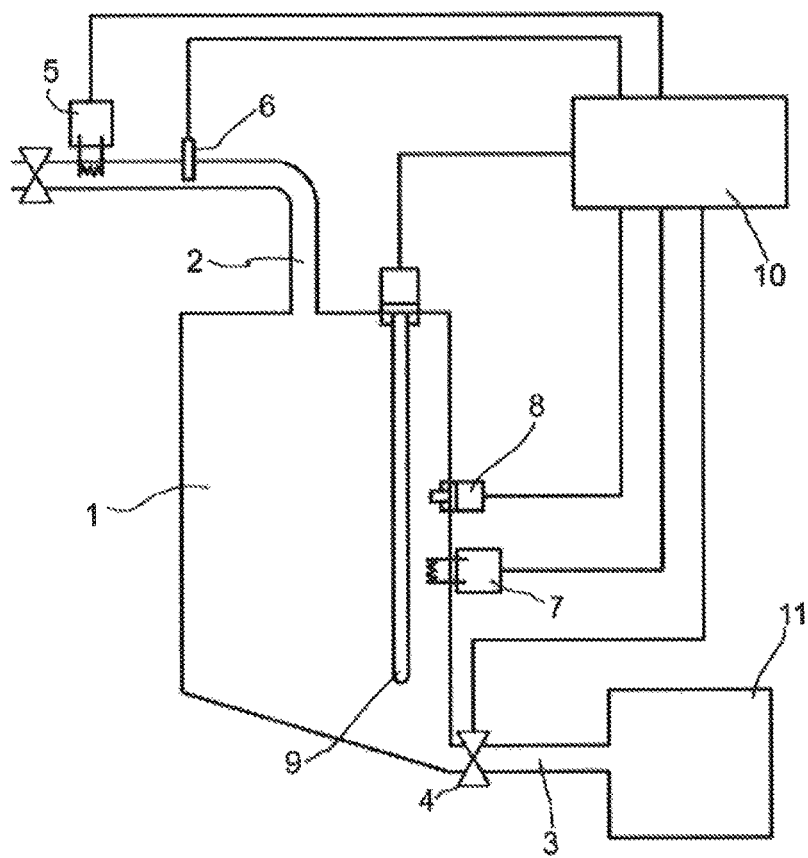

(51) Int. Cl.
*C07C 37/84* (2006.01)
*C07F 5/06* (2006.01)
*B01D 3/10* (2006.01)
*B01D 11/04* (2006.01)
*C07C 29/80* (2006.01)
*C07C 29/17* (2006.01)

(52) U.S. Cl.
CPC .......... *B01D 9/0036* (2013.01); *B01D 9/0063* (2013.01); *B01D 9/0077* (2013.01); *B01D 11/04* (2013.01); *C07C 29/172* (2013.01); *C07C 29/56* (2013.01); *C07C 29/80* (2013.01); *C07F 5/069* (2013.01); *C07B 2200/07* (2013.01); *C07C 2601/14* (2017.05)

(58) Field of Classification Search
CPC ...... B01D 9/004; B01D 9/005; B01D 9/0059; B01D 9/0063; B01D 9/0081; B01D 9/02; B01D 2009/0086; B01D 2009/009; C07C 37/84; C07C 29/172; C07C 29/80; C07C 29/56; C07C 2601/14; C07C 29/78; C07C 35/17; C07C 39/367; C07F 5/069; H05K 999/99; C07B 2200/07; C21D 2281/01
USPC ..... 23/293, 295, 295 R, 296, 297, 300, 301; 210/139, 175, 739, 774
See application file for complete search history.

(56) References Cited

U.S. PATENT DOCUMENTS

| | | | | |
|---|---|---|---|---|
| 4,263,010 | A | * | 4/1981 | Randolph ............ B01D 9/0063 23/295 R |
| 5,463,116 | A | * | 10/1995 | Sumikawa ............ C07C 231/22 562/444 |
| 5,914,012 | A | | 6/1999 | Kaibel et al. |
| 6,315,966 | B1 | * | 11/2001 | Baumgard ........... B01D 9/0013 422/245.1 |
| 7,608,742 | B2 | | 10/2009 | Friedrich et al. |
| 8,003,829 | B2 | | 8/2011 | Heydrich et al. |
| 8,134,034 | B2 | | 3/2012 | Heydrich et al. |
| 8,318,985 | B2 | | 11/2012 | Heydrich et al. |
| 2005/0139484 | A1 | * | 6/2005 | Brooks ................. B01D 9/005 205/687 |
| 2006/0037177 | A1 | * | 2/2006 | Blum ..................... B01D 9/005 23/296 |
| 2010/0249467 | A1 | * | 9/2010 | Heydrich ................ C07C 45/82 568/830 |
| 2014/0256984 | A1 | * | 9/2014 | Myerson ............... C07C 227/42 562/554 |

FOREIGN PATENT DOCUMENTS

| | | |
|---|---|---|
| DE | 2534558 A1 | 2/1977 |
| EP | 0472899 A1 | 3/1992 |
| EP | 0804951 A2 | 11/1997 |
| EP | 1053974 A1 | 11/2000 |
| EP | 1225163 A2 | 7/2002 |
| EP | 2338579 A1 | 6/2011 |
| WO | WO-2006092433 A1 | 9/2006 |
| WO | WO-2008025851 A1 | 3/2008 |
| WO | WO-2008025852 A1 | 3/2008 |
| WO | WO-2009068444 A2 | 6/2009 |

* cited by examiner

METHOD AND DEVICE FOR SEPARATING A SUBSTANCE OUT OF A SOLUTION

CROSS-REFERENCE TO RELATED APPLICATIONS

This application is a national stage application (under 35 U.S.C. § 371) of PCT/EP2015/055279, filed Mar. 13, 2015, which claims benefit of European Application No. 14160645.9, filed Mar. 19, 2014, both of which are incorporated herein by reference in their entirety.

The present invention relates to a method for separating off a substance from a solution. The separation here takes place via a crystallization method. Furthermore, the invention relates to a method for working up an aluminum-containing reaction product from the production of isopulegol by cyclizing citronellal in the presence of complex compounds comprising at least one ligand of the formula (I):

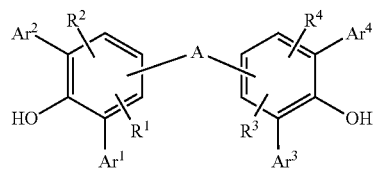

Moreover, the invention relates to a method for producing isopulegol, and to a method for producing menthol.

In terms of amount, menthol is the most important aroma chemical worldwide. The demand for menthol continues to be covered largely by isolation from natural sources. In addition, however, there are also synthetic routes to menthol, sometimes in racemic form, sometimes in the form of the natural enantiomer L-menthol.

An important intermediate for producing racemic such as optically active menthol is isopulegol, which is usually produced by a cyclizing oxo-ene reaction of citronellal in the presence of Lewis-acidic catalysts and is usually produced in the form of mixtures of the four diastereomers isopulegol, iso-isopulegol, neo-isopulegol and neoiso-isopulegol.

Suitable catalysts which have been described for carrying out the abovementioned cyclization of citronellal to isopulegol are both heterogeneous catalysts, such as $SiO_2$, $Al_2O_3/SiO_2$, $SiO_2/ZrO_2$, $SiO_2/TiO_2$ mixed catalysts, mordenites, faujasites, montmorillonites and zeolites—and also homogeneous catalysts, such as, for example, sulfonic acids or Lewis acids, such as, for example, $SnCl_4$, $ZnCl_2$ or $ZnBr_2$.

EP-A 1 225 163 describes the cyclization of citronellal to isopulegol in the presence of tris(2,6-diphenylphenol) aluminum catalysts. This method for cyclizing citronellal to isopulegol uses catalyst complexes which are expensive and can only be produced with complexity. After the described method, to be carried out in a homogeneous phase, the catalyst complex is hydrolyzed when the reaction is complete. Possible recovery and reusability of the ligand liberated in the process is not described.

By contrast, WO 2006/092433 A1 describes bis(diarylphenoxy)-aluminum compounds which are obtainable by reacting a bis(diarylphenol) ligand of the formula (I) with a suitable aluminum compound, and methods of producing isopulegol and menthol in the presence of these compounds. Here, processes are also disclosed which permit recovery of the bis(diarylphenol) ligands of the formula (I) used. Recovery takes place by crystallization from a bottom product obtained during the distillative separation of isopulegol from a reaction product of the cyclization of citronellal. However, such a work-up leads to yields and purities which are not entirely satisfactory, especially in the case of a continuous method for producing isopulegol.

WO 2008/025851 A1 discloses a method for working up an aluminum-containing reaction product from the production of isopulegol by cyclizing citronellal, in which the reaction product is subjected to distillative separation to give an isopulegol-enriched top product and an isopulegol-depleted bottom product, and the ligand is separated off from the bottom product.

Furthermore, WO 2009/068444 A2 discloses a process for producing menthol, in which neral and/or geranial is catalytically hydrogenated to give citronellal, and citronellal is cyclized to isopulegol in the presence of an acidic catalyst. Isopulegol is then purified by crystallization and catalytically hydrogenated to menthol.

In the aforementioned methods, there is a great need to recover the ligands with a high yield. This is because its synthesis is very complex, meaning that the virtually complete recovery of the ligand is of great importance for the economic feasibility of the overall process.

The object of the present invention is therefore to provide a method and a device of the type mentioned at the start in which better efficiency is achieved during the crystallization method, which is used in the course of the method for separating off a substance or for the device for separating off the substance. In this connection, moreover, the time required to obtain the substance should be shortened.

Accordingly, in the method according to the invention for separating off a substance from a solution, electromagnetic radiation is radiated into the solution. An intensity of the electromagnetic radiation which has been scattered by crystals located in the solution is detected and the detected intensity is compared with a desired intensity. The temperature of the solution is then regulated depending on the difference between the detected intensity and the desired intensity such that the amount of this difference is reduced. If the amount of the difference between the detected intensity and the desired intensity is less than a limiting value, a crystallization method is started in which crystals of the substance are obtained which are then separated off.

In this document, a solution is understood as meaning not only a clear solution in which all of the solids are dissolved, but also a particle-laden solution. Such a particle-laden solution is also referred to as suspension. A particle-laden solution can comprise crystals which have formed during the crystallization. During the crystallization, possibly a transition from a clear solution to a particle-laden solution, i.e. a suspension, takes place. Hereinbelow, the terms solution and suspension are therefore used synonymously.

Although the detected intensity here does not include the entire electromagnetic radiation that has been scattered by the crystals located in the solution, but only some of this total scattering intensity, in particular only a fraction proportional to this overall scattering intensity, the change in the crystal surface can be sufficiently ascertained by means of this intensity measurement in order to regulate the temperature for the start of the crystallization process.

It has been found that the crystallization for obtaining the substance takes place only comparatively slowly if the substance to be separated off from the solution has a very complex molecular structure. The formation of new crystal germs and the growth of the crystals take place in such a case only with severe delay. A measure of this is e.g. the supercoolability of the crystallization solution. In the case of a ligand with a complex molecular structure, this can be e.g. up to 50 K, whereas the supercoolability of the solutions of simpler organic molecules is typically only 1 K to 5 K.

Surprisingly, it has now been found that the crystallization of a substance with a complex molecular structure into a readily filterable crystal size and morphology is successful particularly if the crystallization is started with a very precisely measured amount of seed crystals. These seed crystals can then be cultivated to give larger, readily filterable crystals by slowly cooling the solution. Moreover, it has surprisingly been found that the correct amount of seed crystals is present only within a narrow interval and that this amount, to be maintained unusually exactly, can be established relatively easily by means of detecting the intensity of the electromagnetic radiation which has been scattered by the crystals located in the solution. It has been found that the filter resistance changes by more than one order of magnitude if the solution is inoculated too much or too little. On account of the linearity between the filter resistance and the time of filtration or alternatively filter surfaces to be made available, the filtration on the available apparatuses or in the available time becomes impossible if the precisely measured amount of seed crystal at the start of the crystallization method is inappropriate.

The method according to the invention now enables the starting conditions of the crystallization method used in the course of the method according to the invention to be regulated exactly. This means that a desired amount of seed crystals is present at the start of this crystallization method for achieving a crystal size and morphology that is ideal for separating off the crystals by means of the crystallization method.

The stable production and/or preservation of seed crystals in the process presupposes that the connection between the actual concentration of the substance to be crystallized and the associated saturation temperature is precisely known. However, it is a peculiarity of this complex chemical method that, depending on the precise conditions of the preceding reaction, on the actual composition of the worked-up solvent returned in the method and on the concentration of dissolving and nondissolving secondary components that is established, the saturation temperatures of the initially charged solution vary in a wide range e.g. between 85° C. and 115° C. Since, on the other hand, it is empirically known that the temperature at which the seed crystals are produced has to be controlled very precisely, e.g. to 1 K to 3 K, in order to achieve the desired results during the crystallization, an automatic adjustment of these conditions is not possible a priori. The process according to the invention now makes it possible, despite the uncertainties arising from the process, to provide a simple, automatable regulation of the correct inoculation.

A simple method for circumventing the problem of correct inoculation would appear to be to carry out the crystallization continuously. In a state taken to be steady-state, the hot feed solution will be conveyed into the continuously operated crystallizer, the high crystal content of which makes inoculation superfluous. By drawing off a crystal suspension, the introduction of the new solution is balanced out, meaning that such a crystallizer would be operated with an always constant fill level and solids content. However, it has turned out that the extremely great supercoolability of the solutions of substances with a complex molecular structure and the only very sluggish tendency towards crystallization makes such a procedure impossible. Upon introducing the hot feed solution into a cool crystallizer, such a high supersaturation becomes pronounced that it results in the formation of very many, much too small and therefore difficult-to-filter crystals. This difficulty could be reduced by means of a cascading in which a plurality of crystallizers are operated at temperature levels that differ only slightly in each case. The need for a large number of temperature stages and thus a large number of apparatuses, however, makes this process economically disadvantageous.

Moreover, the actual concentration of the substance could be measured with physical or chemical methods, and a saturation temperature and therefore an optimum inoculation temperature could be derived from the composition of the solution. Such a measurement can take place inline e.g. with spectroscopic methods or be performed offline in a chemical laboratory. The latter method, however, signifies an excessively high time expenditure; like the spectroscopic measurement, however, it also fails if a very complex composition of the solution is present. This is because this composition has an effect on the precise dissolution temperature. It is necessary to measure the precise concentration of all of the other ingredients in the solution which, such as e.g. the isopulegol, are able to greatly increase the solubility, or which, like the substance group referred to as "esters", greatly reduce the solubility. Moreover, an exact relationship between the concentration of all components and the saturation temperature that is established would have to be known, which cannot be achieved for a medium with a complex composition.

If determination by measurement of the relationship between the concentration and the saturation temperature is not possible, then the empirical determination of the saturation temperature could be a way out. For example, the saturation temperature of such a solution can be determined by means of targeted supercooling of the solution, forcing crystal formation at sometimes high supercooling and reheating the solution while determining the dissolution temperature of the last crystal. This method can also take place again laboriously on a sample in the laboratory; it is also conceivable to carry out this measurement automated by any desired measuring system in the bypass to the actual crystallizer. In the event of high supercoolability of the solution and on account of the need to warm the solution very slowly in order to precisely determine the saturation temperature, such a determination would last at least many hours and would therefore be economically disadvantageous.

In the method according to the invention, for the automated adjustment of the initially available amount of seed crystals, an optical measurement method is used in conjunction with a regulation of the starting conditions for the crystallization method used in the course of the method. Here, electromagnetic radiation is radiated into the solution and the electromagnetic radiation back-scattered by any crystals present is detected. This back-scattering for crystals that are considerably larger than the wavelength of the radiated electromagnetic radiation is in first approximation proportional to the amount of crystal surface present in the suspension. In the process according to the invention, it is thus not the mass of crystals that is ascertained at the start of the crystallization process, but the crystal surface. As a result of this, an even better crystal growth and thus an even higher yield and a lower time expenditure can be achieved for separating off the crystals since it is not the mass of crystals that is important for the success of the crystallization, but the crystal surface provided for accommodating supersaturation. For this reason, the measurement of the crystals by means of the electromagnetic radiation for regulating the conditions at the start of the crystallization method is particularly advantageous.

The limiting value for the amount of difference between the detected intensity and the desired intensity is a tolerated deviation from the desired intensity. This limiting value can be for example 5% or 20% of the desired intensity. However, the limiting value can also be determined on the basis of absolute deviations from the desired intensity. If the target value is e.g. 0.1, the target range of 0.15 to 0.1 could thus be chosen. By contrast, if the target value is 0.5, then the target range selected would be from 0.55 to 0.5.

According to one embodiment of the method according to the invention, the crystalline substance is separated off by filtration. During regulation of the starting conditions of the crystallization method, a desired intensity was selected which provides a crystal surface which leads to a crystal size and morphology which is particularly preferred for the filtration. In this way, a particularly high yield and a lower time expenditure for separating off the crystals from the solution are achieved. Furthermore, the crystalline substance can also be isolated, i.e. separated off, from the solution by floatation, centrifugation or sieving.

According to a further embodiment of the method according to the invention, the desired intensity is determined by reference measurements. At these reference measurements, the relationship between the crystal size and/or the crystal morphology at the end of the crystallization method and of the detected intensity at the start of the crystallization method is determined for the solution. From this, the desired intensity selected is that intensity which is assigned to the desired crystal size and/or crystal morphology. In this way, it can be determined in advance what intensity of the back-scattered electromagnetic radiation corresponds to the ideal starting conditions for the crystallization method under which the desired crystals are cultivated for the subsequent separation. The desired intensity determined in this way then corresponds to an ideal crystal surface in a solution volume. This in turn corresponds to approximately one crystal concentration. On the basis of this desired intensity of the back-scattered electromagnetic radiation, the temperature for the start of the crystallization method can therefore be regulated in the process according to the invention. Advantageously, this can take place without detailed knowledge of the concentration of the substance to be crystallized or of the amount of dissolving or nondissolving substances.

According to one development of the process according to the invention, the solution or some of the solution is brought in a crystallization vessel to a temperature which is lower than a defined starting temperature value, which is below the anticipated saturation temperature of the solution. The solution is then heated until the amount of difference between the detected intensity and the desired intensity is less than the limiting value. The solution is in particular brought to a temperature far below the anticipated saturation temperature, so that a large number of crystals of the substance to crystallize form spontaneously. In this way, seed crystals are obtained in situ. In this embodiment of the method according to the invention, the temperature of the solution is thus regulated from lower temperatures to higher temperatures in order to obtain an ideal starting temperature for the crystallization method. During this regulation, the amount of crystal present is initially very much greater than desired. Moreover, the crystal size and morphology does not correspond to the desired crystal size and morphology. By increasing the temperature during the regulation, crystals then dissolve until the detected intensity of the back-scattered electromagnetic radiation indicates that the desired crystal surface is present in the solution. If during this regulation too low a detected intensity arises, this can be counteracted by lowering the temperature for the solution since the crystal surface is then enlarged again.

The starting temperature value is in particular at least 10 K below the anticipated saturation temperature of the solution. On the other hand, the starting temperature value can also be determined from the desired intensity. For example, the starting intensity assigned to the starting temperature value is selected as the x-fold intensity of the desired intensity, where the value x is in a range from 1.2 to 10. In particular, the value x is in a range from 3 to 10, preferably in a range from 4 to 9 and particularly preferably in a range from 6 to 9. The temperature of the solution is then regulated in such a way until the detected intensity is greater than the starting intensity. By means of this procedure, it can advantageously be ensured in a very simple manner that firstly an adequately large amount of crystals is present in the solution, which is then successively reduced during the regulation, until the desired intensity, i.e. the ideal starting temperature for the start of the crystallization process, is present.

According to one embodiment of the method according to the invention, the supercoolability of the solution used is greater than 5 K, in particular greater than 10 K or greater than 30 K. In such cases, the implementation of the crystallization method is particularly critical as regards the formation of crystals which are suitable for subsequent filtration. In these cases, it is therefore particularly important that the starting conditions, i.e. in particular the crystal surface at the start of the crystallization method, are ideal for the crystal growth during the crystallization method. By virtue of the method according to the invention, the radiation of the electromagnetic radiation and the measurement of the intensity of the back-scattered radiation can ensure that ideal conditions are present at the start of the crystallization.

According to one embodiment of the method according to the invention, the electro-magnetic radiation of one wavelength range or two or more wavelength ranges which is/are wider than 20 nm (e.g. 740 nm to 760 nm), is irradiated into the solution or suspension which is greater than 20 nm. The irradiated electromagnetic radiation thus comprises different wavelengths which extend at least over a range of 20 nm. Hence, what is irradiated is in particular not like during laser radiation monochromatic light or monochromatic radiation, i.e. radiation in a very narrow frequency range, but light or radiation of different wavelengths. The wavelength range can in particular also be very much wider and extend over 50 nm, 100 nm or more nm.

The electromagnetic radiation irradiated into the solution or suspension has the form of a beam. According to one embodiment of the method according to the invention, the minimum cross section of this beam is greater than 0.1 mm, in particular greater than 0.19 mm and preferably greater than 0.39 mm. Furthermore, the beam is in particular divergent, i.e. it has an aperture angle. This aperture angle is e.g. greater than 5°, in particular greater than 10° and preferably greater than 20°. Since the cross section of such a divergent beam increases in the direction of radiation, the minimum cross section of such a beam is the cross section of the beam upon entry into the solution or suspension.

The radiated electromagnetic radiation can be for example in the visible spectral range. Preferably, however, infrared radiation is radiated into the solution. Accordingly, the intensity of infrared radiation is detected. The infrared radiation can be for example in a wavelength range from 780 nm to 1000 nm, in particular in a range from 800 nm to 900 nm and preferably in a range from 820 nm to 880 nm. The wavelength of the radiated electromagnetic radiation corresponds here to the wavelength of the detected, back-scattered radiation.

According to a preferred embodiment of the method according to the invention, the electromagnetic radiation is radiated into the solution by means of a scattered-light probe. Equally, the intensity of the back-scattered electromagnetic radiation is detected by means of the scattered-light probe. Here, in particular the incident direction of the radiated electromagnetic radiation is essentially parallel to the detection direction from which the intensity of the back-scattered electromagnetic radiation is detected. This prevents electromagnetic radiation radiated into the solution from being detected directly without this radiation having been scattered at crystals.

In the method according to the invention, as a result of the above-characterized irradiation of the electromagnetic radiation into the solution or suspension, in particular by means of a scattered-light probe, through detection of the intensity of the electro-magnetic radiation that has been scattered by crystals located in the solution or suspension, a signal can be obtained which is proportional to the particle surface of a particle collective in the solution or suspension. By virtue of this signal it is possible to adjust the starting temperature for the start of the crystallization method in a particularly accurate manner since, as a result of this, the amount of seed crystals initially available can be ascertained very precisely.

The method according to the invention here has essential advantages compared to a measurement of the particle size distribution and the particle number, as are obtained for example also via FBRM (focused beam reflectance measurement) methods. In the FBRM method, the particle size distribution is not ascertained directly, but via a so-called cord length distribution. For this, a laser beam is radiated into the solution with the particles. The laser beam has a very small cross section of a few micrometers. Furthermore, it rotates at a constant speed of about 2 m/s. Particles affected by the rotating laser beam are scanned in this way. The electromagnetic radiation which are detected by a sensor as a result of reflection of the laser beam at the particles is measured. The pregiven rotational speed at which the laser beam is moving and the pulse times are then used to calculate cord length distributions. The literature refers to the fact that the calculation of a particle size distribution from the cord length distribution is very complex and fraught with errors. For example, errors arise while calculating the cord length distributions depending on the relative speed of the particles streaming by.

If the particle speed approaches zero, errors additionally arise in the particle counting rate since virtually all of the particles are measured several times with different cord lengths. Moreover, the rotating focus of the laser beam, only a few micrometers in size, which is radiated into the solution or suspension, and of the beam which arrives at the detector after reflection lies very close to the disk of the sensor head. The result of this is that further removed particles lead, on account of the optical beam path to significantly lower-intensity signals with lower edge steepness. If a minimum edge steepness is not reached, these signals are discarded since the required spatial resolution is no longer present. Since at a very low number of particles per spatial volume, only very few particles per unit of time stay directly at the sensor head and can thus be scanned by the rotating focus point of the laser beam, only very low count rates are achieved in this case too. Even if the minimum edge steepness is set as parameter to a very low value, further removed particles cannot be detected since the signal processing electronics is designed for a high limiting frequency in order to ensure a high time-wise resolution of the signal. The signal processing electronics is in this case not designed for a high light sensitivity. The FBRM method was therefore developed for moderate to high particle concentrations.

In the FBRM method, at best a particle number in the solution or suspension can thus be determined. A reliable measurement of the particle size distribution is not possible since this particle size distribution is only obtained from a cord length distribution and the conversion of this distribution to a particle size distribution is fraught with errors and assumptions are made. Thus it is necessary, for example, to take as a basis a model of the three-dimensional geometric shapes of the particles in question.

In the method according to the invention in which the radiated electromagnetic radiation has the aforementioned features, this radiation being generated in particular by a so-called scattered-light probe, the surface of particle collectives in the suspensions can be measured with a very low to a very high number of particles per spatial volume. In this connection, it is possible to detect only the intensity, i.e. in particular the total intensity, of the electromagnetic radiation that has been scattered by crystals located in the solution. In the FBRM method, no direct intensity measurement is carried out. The reason for this is that in this method the intensification of the signal processing electronics is adjusted differently for each particle type so that neither an excessively high nor an excessively low signal is detected. This is because in the FBRM method, it is a question only of the number and duration of light pulses which arise from the reflection at the particles, but in no way the intensity of the reflected radiation.

In the method according to the invention for separating off a substance from a solution or suspension in which the crystal concentration is to be regulated to a very low value in order to attain a certain particle surface, the measurement method is by means of the scattered-light probe or by means of electromagnetic radiation which has the aforementioned features, better suited than the FBRM method since it has a higher sensitivity. Moreover, it is very much more cost effective to implement. The complexity which has to be operated during the detection is very much lower since only one integral intensity signal has to be captured.

According to one embodiment of the method according to the invention, the solution (suspension) is introduced into a crystallization vessel at a temperature which is below the starting temperature value. The introduced solution thus has a large crystal amount. If the scattered-light probe is located within the introduced solution, i.e. if the crystallization vessel is filled so much that the fill level of the solution is above the scattered-light probe, the electromagnetic radiation is radiated into the solution by means of the scattered-light probe and the intensity of the electromagnetic radiation that has been scattered by the crystals located in the solution is detected. The temperature of the solution is then regulated upon further introduction of the solution into the crystallization vessel such that the amount of the difference between the detected intensity and the desired intensity is less than the limiting value. In the ideal case, in this procedure, in the event of complete filling of the crystallization vessel the detected intensity is the same as the desired intensity and the amount of difference between these intensities is less than the limiting value, meaning that in the event of complete filling of the crystallization vessel the desired amount of seed crystal is present.

In this way, the time expenditure for carrying out the process according to the invention can be shortened. If, after the complete filling of the crystallization vessel, the amount of difference between the detected intensity and the desired intensity is still greater than the limiting value, a fine adjustment of the temperature can also be used to bring the detected intensity closer to the desired intensity such that the difference in the amount is below the limiting value and consequently the desired seed crystal amount is then present.

In this specification, the crystallization method which is used in the course of the method according to the invention for separating off the substance from the solution is the part of the method which starts when the amount of difference between the detected intensity and the desired intensity is less than a limiting value although crystals have also formed in the preceding parts of the method.

The crystallization method which is used in the course of the method according to the invention for separating off the substance from the solution is in particular a cooling crystallization process. After the temperature of the solution has been thus regulated such that the amount in the difference between the detected intensity and the desired intensity is less than the limiting value, the solution is then slowly cooled again so that, supported by the seed crystals obtained in situ, larger crystals are again formed. The cooling rate here is firstly relatively slight, later on, when larger crystals have already formed, the cooling rate can also be increased to accelerate the method.

The invention further relates to a method for obtaining a substance from a solution by means of crystallization, in which the solution is introduced into a first crystallization vessel and the substance is separated off by means of crystallization in the first crystallization vessel by the method described above. While carrying out the crystallization method in the first crystallization vessel, the solution is introduced into a second crystallization vessel and the substance is separated off by means of crystallization in the second crystallization vessel by the process described above. Consequently, while carrying out the crystallization method in the first crystallization vessel, e.g. by means of a cooling crystallization, the same method is started in the second crystallization vessel from the start. In this way, the method for separating off the substance from the solution can essentially be continuously operated since during the crystallization in the one crystallization vessel the solution is introduced into the other crystallization vessel and in so doing the regulation is carried out in order to ensure that the desired crystal surface is present for the start of the crystallization method in the second crystallization vessel. Optionally, further crystallization vessels can also be connected in parallel. The number of crystallization vessels is for example governed by how much time is needed in order to produce the desired starting conditions for the crystallization process, and how long the actual crystallization process then requires. In this connection, the number of crystallization vessels can for example be selected such that solution is introduced into crystallization vessels until the crystallization method in the first crystallization vessel has concluded and the solution can be introduced into this again.

The invention further relates to a device for separating off a substance from a solution. The device has at least one crystallization vessel which comprises an opening for introducing the solution. Furthermore, the device comprises a heating device for changing the temperature of the solution to be introduced and/or introduced. Furthermore, a temperature sensor is provided for measuring the temperature of the solution to be introduced and/or introduced. Arranged within the crystallization vessel is a scattered-light probe with which electromagnetic radiation can be radiated into the solution and an intensity of the electromagnetic radiation which has been scattered by crystals present in the solution can be detected. The device further comprises a regulating unit which is data-coupled with the temperature sensor, the scattered-light probe and the heating device. Using this regulating unit, the temperature of the solution in the crystallization vessel can be regulated such that the amount of difference between the detected intensity and a desired intensity is reduced. If the amount of the difference between the detected intensity and the desired intensity is less than a limiting value, a crystallization process can be actuated. Crystals of the substance are obtained by the crystallization method. Finally, the device comprises a separation unit for separating off the resulting crystals.

The heating device is in particular arranged in the line via which the solution is fed to the crystallization vessel. In this way, the temperature of the introduced solution can be regulated.

The temperature sensor is in particular arranged in the crystallization vessel so that the temperature of the solution located in the crystallization vessel is measured. Additionally, a temperature sensor is also preferably provided in the line via which the solution is conveyed to the crystallization vessel.

The scattered-light probe has in particular an emitter for infrared radiation. The radiation emitted by the emitter is introduced into the crystallization vessel via a waveguide. Here, the decoupling area of the waveguide is arranged in the lower section of the crystallization vessel so that above a certain fill level electromagnetic radiation is radiated into the solution. Similarly, the scattered-light probe has in particular a coupling area of a further waveguide in the crystallization vessel. The scattered light coupled via the coupling area is passed to a detector of the scattered-light probe via the other waveguide.

According to one embodiment of the device according to the invention, the electro-magnetic radiation radiated by the scattered-light probe is in one wavelength range or several wavelength ranges which is/are wider than 20 nm. The wavelength range or ranges can in particular, however, also be wider than 50 nm or 100 nm. According to a further embodiment of the device according to the invention, the beam that can be produced by the scattered-light probe has a minimum cross section greater than 0.1 mm, in particular greater than 0.39 mm. Furthermore, the beam preferably has an aperture angle greater than 5°, preferably greater than 10° and in particular greater than 20°.

By means of the regulating unit, the crystallization process is carried out in particular in such a way that the solution is cooled, so that crystals of the substance are obtained. To separate off the crystals obtained, the separating-off unit is configured such that the crystals can be isolated from the solution by filtration, floatation, centrifugation or sieving.

The device according to the invention is in particular configured to carry out the above-described method according to the invention. It therefore has the same advantages as the method.

According to a development of the device according to the invention, it comprises two crystallization vessels. In this case, a heating device, a temperature sensor and a scattered-light probe are provided for both crystallization vessels. The regulating unit in this case controls the introduction of solvent in such a way that while carrying out the crystallization method in the first crystallization vessel the solution is introduced into the second crystallization vessel and subsequently the crystallization method is then also carried out in the second crystallization vessel.

The present invention additionally provides a method for working up an aluminum-containing reaction product from the production of isopulegol by cyclizing citronellal, comprising
i) isopulegol,
ii) at least one ligand of the formula (I),

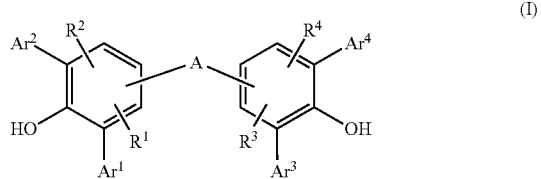

where
Ar$^1$, Ar$^2$, Ar$^3$, Ar$^4$, independently of one another, are chosen from C$_6$-C$_{15}$-aryl radicals or C$_2$-C$_{15}$-heteroaryl radicals, which, if appropriate, can in each case carry 1 to 7 identical or different substituents chosen from C$_1$-C$_6$-alkyl, C$_1$-C$_6$-perfluoroalkyl, C$_1$-C$_6$-alkoxy, C$_7$-C$_{12}$-aralkyl, halogen, SiR$^{5a}$R$^{6a}$R$^{7a}$, optionally substituted C$_6$-C$_{10}$-aryl, NR$^{8a}$R$^{9a}$, SR$^{10b}$, NO$_2$, R$^1$, R$^2$, R$^3$, R$^4$, independently of one another, are chosen from hydrogen, C$_1$-C$_6$-alkyl, C$_1$-C$_6$-perfluoroalkyl, C$_1$-C$_6$-alkoxy, C$_7$-C$_{12}$-aralkyl, halogen, SiR$^{5b}$R$^{6b}$R$^{7b}$, optionally substituted C$_6$-C$_{10}$-aryl, NR$^{8b}$R$^{9b}$, SR$^{10b}$, NO$_2$ and where R$^1$ or R$^2$ and/or R$^3$ or R$^4$, together with A, can form an aromatic or nonaromatic cycle, and A is a straight-chain or branched and/or cyclic hydrocarbon radical having 1 to carbon atoms which may be saturated or mono- or polyunsaturated and/or partially aromatic and can, if appropriate, have one or more identical or different heteroatoms chosen from O, S, NR$^{11}$, and/or one or more identical or different functional groups chosen from the functional groups C(O), S(O), S(O)$_2$ and can, if appropriate, carry one or more identical or different substituents chosen from the substituents C$_1$-C$_6$-alkyl, C$_1$-C$_6$-perfluoroalkyl, C$_1$-C$_6$-alkoxy, C$_1$-C$_{10}$-acyloxy, C$_7$-C$_{12}$-aralkyl, halogen, —SiR$^{5c}$R$^{6c}$R$^{7c}$, optionally substituted C$_6$-C$_{10}$-aryl, substituted or unsubstituted C$_2$-C$_{10}$-hetaryl, NR$^{8c}$R$^{9c}$, SR$^{10c}$, NO$_2$, C$_1$-C$_{12}$-acyl, C$_1$-C$_{10}$-carboxyl, or is a C$_6$-C$_1$-aryl radical or a C$_2$-C$_{15}$-heteroaryl radical which can, if appropriate, in each case carry 1 to 5 substituents chosen from C$_1$-C$_6$-alkyl, C$_1$-C$_6$-perfluoroalkyl, C$_1$-C$_6$-alkoxy, C$_7$-C$_{12}$-aralkyl, halogen, SiR$^{5d}$R$^{6d}$R$^{7d}$, substituted or unsubstituted C$_6$-C$_{10}$-aryl, NR$^{8d}$R$^{9d}$, SR$^{10d}$, NO$_2$, or is a functional group or a heteroatom chosen from the group —O—, —S—, —N(R$^{11}$)—, —S(O)—, —C(O)—, —S(O)$_2$—, —P(R$^{11}$)—, —(R$^{11}$)P(O)— and —Si(R$^{12}$R$^{13}$), where the radicals R$^{5a}$, R$^{6a}$, R$^{7a}$, R$^{8a}$, R$^{9a}$, R$^{10a}$ to R$^{5d}$, R$^{6d}$, R$^{7d}$, R$^{8d}$, R$^{9d}$, R$^{10d}$, R$^{11}$, R$^{12}$ and R$^{13}$ are in each case independently of one another chosen from C$_1$-C$_6$-alkyl, C$_7$-C$_{12}$-aralkyl and/or substituted or unsubstituted C$_6$-C$_{10}$-aryl and where the radicals R$^{8a}$ and R$^{9a}$, R$^{8b}$ and R$^{9b}$, R$^{8c}$, and R$^{9c}$, R$^{8d}$ and R$^{9d}$, independently of one another, can in each case together also form a cyclic hydrocarbon radical having 2 to 8 carbon atoms which can have one or more identical or different heteroatoms chosen from the group O, S, NR$^{11a}$, and R$^{11a}$ can have the meanings given for R$^{11}$, in free and/or complex-bound form,
in which
a) the aluminum-containing reaction product is subjected to distillative separation to obtain an isopulegol-enriched top product and an isopulegol-depleted bottom product,
b) the isopulegol-depleted bottom product is brought into close contact with an aqueous base to give an aluminum-containing aqueous phase and an organic phase comprising the majority of the ligands of the formula (I),
c) the ligands of the formula (I) are separated off from the organic phase.

The bis(diarylphenol) ligands of the formula (I) obtained by the method according to the invention can usually be converted to the reactive catalyst complex without further purification steps, within the scope of a new batch with the corresponding aluminum compounds of the formulae (II) or (III), as defined below, with no or no noteworthy decrease in the reactivity being established with catalyst complexes recovered in this way.

The bis(diarylphenol) ligands of the formula (I) have two phenol systems which in each case are substituted in both ortho positions relative to the phenolic hydroxy group by aromatics or heteroaromatics (Ar$^1$ to Ar$^4$) and are joined together via a structural element A and can, if appropriate, also carry further substituents (R$^1$ to R$^4$).

The aromatic or heteroaromatic substituents Ar$^1$ to Ar$^4$ may, independently of one another, be identical or different. Preferably, the two substituents bonded in each case to a phenol system (Ar$^1$ and Ar$^2$ or Ar$^3$ and Ar$^4$) are pairwise identical. Particularly preferably, all four substituents Ar$^1$ to Ar$^4$ are identical.

The specified substituents Ar$^1$ to Ar$^4$ are aryl radicals having 6 to 15, preferably 6 to 10, carbon atoms or heteroaryl radicals having 2 to 15, preferably 3 to 10, carbon atoms in the aromatic ring system. Aryl radicals having 6 to 15 carbon atoms are, for example, phenyl, naphthyl, anthracenyl, preferably phenyl and naphthyl.

The specified heteroaryl radicals having 2 to 15 carbon atoms have 1 to about 6, generally 1 to 3, identical or different heteroatoms which are chosen from the group of heteroatoms O, S and N. Examples thereof which may be mentioned are the following heteroaryl radicals: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, benzofuryl, isobenzofuryl, benzothienyl, indolyl, isoindolyl, carbazolyl, pyridyl, quinolyl, isoquinolyl and pyrazyl. Preferred heteroaryl radicals are, for example: 2-furyl, 2-pyridyl, 2-imidazoyl.

The aryl or heteroaryl radicals specified above for $Ar^1$ to $Ar^4$ can, in each case independently of one another, be unsubstituted or carry 1 to about 7, preferably 1 to 3, in particular 1 or 2, identical or different substituents which are chosen from the group of substituents: $C_1$-$C_6$-alkyl, $C_1$-$C_6$-perfluoroalkyl, $C_1$-$C_6$-alkoxy, $C_7$-$C_{12}$-aralkyl, halogen, —$SiR^{5a}R^{6a}R^{7a}$, substituted or unsubstituted $C_6$-$C_{10}$-aryl, —$NR^{8a}R^{9a}$, —$SR^{10a}$, —$NO_2$, where the radicals $R^{5a}$, $R^{6a}$, $R^{7a}$, $R^{8a}$, $R^{9a}$, $R^{10a}$ and $R^{11}$ to $R^{13}$, in each case independently of one another, are $C_1$-$C_6$-alkyl, $C_7$-$C_{12}$-aralkyl and/or substituted or unsubstituted $C_6$-$C_{10}$-aryl, and the radicals $R^{8a}$ and $R^{9a}$, independently of one another can in each case together also form a cyclic hydrocarbon radical having 2 to 8 carbon atoms which can have one or more identical or different heteroatoms chosen from the group O, S and $NR^{11a}$, and $R^{11a}$ can have the meanings given for $R^{11}$.

In this connection, the specified substituents within the scope of the overall present invention have the meanings given below by way of example:

$C_1$-$C_6$-alkyl such as, for example, methyl, ethyl, propyl, 1-methylethyl, butyl, 1-methylpropyl, 2-methylpropyl, 1,1-dimethylethyl, pentyl, cyclopentyl, 1-methylbutyl, 2-methylbutyl, 3-methylbutyl, 2,2-dimethylpropyl, 1-ethylpropyl, hexyl, cyclohexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethyl-butyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl and 1-ethyl-2-methylpropyl;

$C_1$-$C_6$-perfluoroalkyl, such as, for example, trifluoromethyl, pentafluoroethyl, heptafluoropropyl, heptafluoroisopropyl, nonafluorobutyl;

$C_1$-$C_6$-alkoxy, such as, for example, methoxy, ethoxy, propoxy, 1-methylethoxy, butoxy, 1-methylpropoxy, 2-methylpropoxy and 1,1-dimethylethoxy, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_7$-$C_{12}$-aralkyl, such as, for example, benzyl, 1-phenylethyl, 2-phenylethyl;

$C_1$-$C_{10}$-acyloxy, such as, for example, acetyloxy, propionyloxy;

$C_1$-$C_{10}$-carboxyl, such as, for example, methoxycarbonyl, ethoxycarbonyl, propyloxycarbonyl, isopropyloxycarbonyl;

$C_1$-$C_{10}$-acyl, such as, for example, formyl, acetyl, propionyl.

The expression "substituted or unsubstituted $C_6$-$C_{10}$-aryl" within the meaning of the present invention is aryl radicals which, as specified above, have one or more, generally 1 to about 3, identical or different substituents, where the substituents may be chosen, for example, from $C_1$-$C_6$-alkyl, $C_1$-$C_6$-perfluoroalkyl, $C_1$-$C_6$-alkoxy, $C_7$-$C_{12}$-aralkyl, halogen, silyl, dialkylamino and nitro.

Within the scope of the present invention, the term "halogen" is fluorine, chlorine, bromine and iodine, preferably fluorine and chlorine.

Within the scope of the present invention, the substituents —$SiR^{5a}R^{6a}R^{7a}$ to —$SiR^{5d}R^{6d}R^{7d}$ are in each case understood as meaning silyl substituents each having, independently of one another, three identical or different radicals which are chosen from the radicals $C_1$-$C_6$-alkyl, $C_7$-$C_{12}$-aralkyl and substituted or unsubstituted $C_6$-$C_{10}$-aryl. By way of example, mention may be made here, for example, of the silyl substituents trimethylsilyl, triethylsilyl, tert-butyldimethylsilyl and tert-butyldiphenylsilyl.

Within the scope of the present invention, the substituents —$NR^{8a}R^{9a}$ to —$NR^{8d}R^{9d}$ are in each case amino substituents which, in each case independently of one another, carry two identical or different, preferably two identical, radicals which are chosen from the abovedescribed radicals $C_1$-$C_6$-alkyl, $C_7$-$C_{12}$-aralkyl and/or substituted or unsubstituted $C_6$-$C_{10}$-aryl. By way of example, mention may be made of the amino substituents: dimethylamino, diethylamino, dibenzylamino, diallylamino, diisopropylamino. Within the scope of the present invention, the radicals $R^{8a}$ and $R^{9a}$ to $R^{8d}$ and $R^{9d}$ may independently of one another, in each case together also form a cyclic hydrocarbon radical having 2 to 8 carbon atoms which can have one or more identical or different heteroatoms chosen from the group O, S, $NR^{11a}$. The radical $R^{11a}$ can here be abovedescribed $C_1$-$C_6$-alkyl, $C_7$-$C_{12}$-aralkyl and/or substituted or unsubstituted $C_6$-$C_{10}$-aryl. Examples of these cyclic substituents $R^{8a}$ and $R^{9a}$ to $R^{8d}$ and $R^{9d}$ which may be mentioned are: piperidinyl, morpholinyl, N-methylpiperazinyl, N-benzylpiperazinyl.

In the substituents —$SR^{10a}$, the radical $R^{10a}$ is an abovedefined $C_1$-$C_6$-alkyl, $C_7$-$C_{12}$-aralkyl and/or substituted or unsubstituted $C_6$-$C_{10}$-aryl, preferably methyl, ethyl, isopropyl, phenyl, benzyl.

Within the scope of the present invention, preferred aromatic or heteroaromatic substituents $Ar^1$, $Ar^2$, $Ar^3$, $Ar^4$ are, for example, phenyl, 4-methylphenyl, 2,4,6-tri-methylphenyl, naphthyl, 2-fluorophenyl, 4-fluorophenyl, 4-chlorophenyl, 4-bromophenyl, 3-fluorophenyl, 3-chlorophenyl, 3,5-difluorophenyl, 3,5-dichlorophenyl, 2,3,6-trichloro-phenyl, 2,4,6-trichlorophenyl, 2-methylphenyl, 4-methylphenyl, 2,4,5-trimethylphenyl, 2,4,6-trimethylphenyl. 2-isopropylphenyl, 4-isopropylphenyl, 4-tert-butylphenyl, 4-n-butylphenyl, 3-trifluoromethylphenyl, 4-trifluoromethylphenyl, 3,5-bis(trifluoro-methyl)phenyl, 4-arylphenyl, 3-nitrophenyl, preferably 4-fluorophenyl, 4-chlorophenyl, 3-chlorophenyl, 3,5-dichlorophenyl, 3-trifluoromethylphenyl, 4-trifluoromethylphenyl. Within the scope of a preferred embodiment, the radicals $Ar^1$, $Ar^2$, $Ar^3$, $Ar^4$ are identical and are preferably 4-fluorophenyl, 4-chlorophenyl, 3-chlorophenyl, 3,5-dichlorophenyl, 3-trifluoromethylphenyl, 4-trifluoromethylphenyl, particularly preferably phenyl.

According to the invention, the substituents $R^1$, $R^2$, $R^3$, $R^4$ in the meta or para position relative to the respective phenolic hydroxy groups may be identical or different, preferably identical, and, in each case independently of one another, are hydrogen and/or an abovementioned $C_1$-$C_6$-alkyl, $C_1$-$C_6$-perfluoroalkyl, $C_1$-$C_6$-alkoxy, $C_7$-$C_{12}$-aralkyl, halogen, —$SiR^{5b}R^{6b}$, $R^{7b}$, substituted or unsubstituted $C_6$-$C_{10}$-aryl, —$NR^{8b}R^{9b}$, —$SR^{10b}$ and/or —$NO_2$.

Preferred radicals $R^1$, $R^2$, $R^3$, $R^4$ which may be mentioned are: methyl, ethyl, isopropyl, halogen, in particular fluorine and/or chlorine, trifluoromethyl, phenyl, methoxy, nitro. Preferably, the radicals $R^1$, $R^2$, $R^3$, $R^4$ are identical and are particularly preferably hydrogen.

The radicals $R^1$ or $R^2$ and/or $R^3$ or $R^4$ may, together with the structural element A, also form a cyclic aromatic or nonaromatic cycle. In these cases, the bis(diarylphenol) ligands of the formula (I) to be used according to the invention have a tricyclic basic structure, for example an anthracene basic structure of the formula (X) or basic structures of the type (XI):

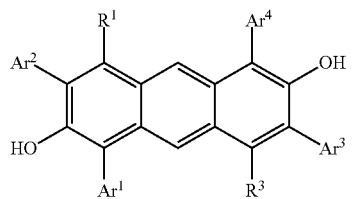

(X)

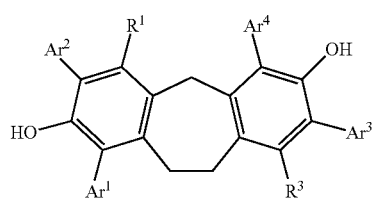

(XI)

Further structural modifications of these tricyclic basic structures, if appropriate also those which have heteroatoms in the basic structure, are known to the person skilled in the art and belong to the group of bis(diarylphenol) ligands which can be used according to the invention.

The structural element A in formula (I) can be a straight-chain or branched and/or cyclic hydrocarbon radical having 1 to 25 carbon atoms, which may be saturated or mono- or polyunsaturated, normally 1 to about 6-fold unsaturated and/or may be partially aromatic. The specified hydrocarbon radicals can, if appropriate, have one or more, generally 1 to 3, identical or different heteroatoms chosen from the group of hetero-atoms O, S and $NR^{11}$ and/or one or more identical or different functional groups chosen from the group of functional groups C(O), S(O) and $S(O)_2$, and if appropriate carry one or more identical or different substituents chosen from the group of the substituents $C_1$-$C_6$-alkyl, $C_1$-$C_6$-perfluoroalkyl, $C_1$-$C_6$-alkoxy, $C_1$-$C_{10}$-acyloxy, $C_7$-$C_{12}$-aralkyl, halogen, —$SiR^{5c}R^{6c}R^{7c}$, substituted or unsubstituted $C_6$-$C_{10}$-aryl, substituted or unsubstituted $C_2$-$C_{10}$-hetaryl, —$NR^{8c}R^{9c}$, —$SR^{10c}$, —$NO_2$, $C_1$-$C_{12}$-acyl and $C_1$-$C_{10}$-carboxyl.

Preferably, the structural element A in formula (I) is a straight-chain or branched and/or cyclic hydrocarbon radical having 1 to 25, preferably 1 to 15 and particularly preferably 1 to 10, carbon atoms, which may be saturated or mono- to triunsaturated and/or partially aromatic. The preferred hydrocarbon radicals can, if appropriate, have one or more, generally 1 to 3, identical or different heteroatoms chosen from the group of heteroatoms O, S and $NR^{11}$ and/or one or more C(O) groups and, if appropriate, carry one or more identical or different substituents chosen from the group of substituents $C_1$-$C_6$-alkyl, $C_1$-$C_6$-perfluoroalkyl, $C_1$-$C_6$-alkoxy, $C_1$-$C_{10}$-acyloxy, $C_7$-$C_{12}$-aralkyl, halogen, substituted or unsubstituted $C_6$-$C_{10}$-aryl, —$NO_2$, $C_1$-$C_{12}$-acyl and $C_1$-$C_{10}$-carboxyl.

Examples of structural elements A in the formula (I) which may be mentioned without any limiting character are the following structural elements 1 to 44, where the wavy lines in each case mark, as within the scope of the overall present disclosure, the linkage sites to the remainder of the particular ligand structure:

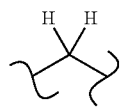

1

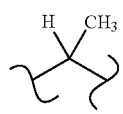

2

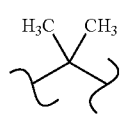

3

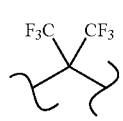

4

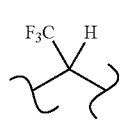

5

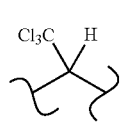

6

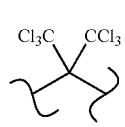

7

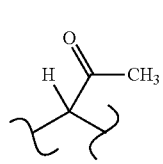

8

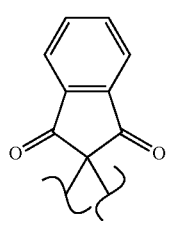

9

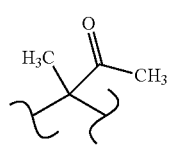

10

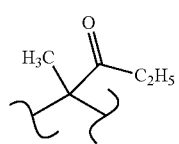

11

-continued
| | |
|---|---|
| 12 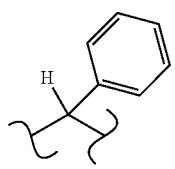 | 20 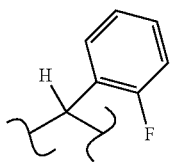 |
| 13 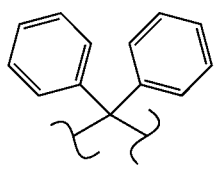 | 21 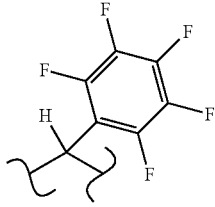 |
| 14 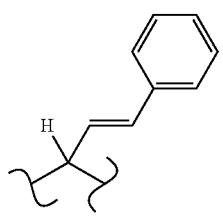 | 22 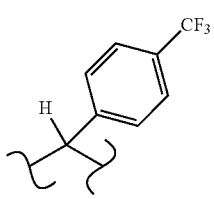 |
| 15 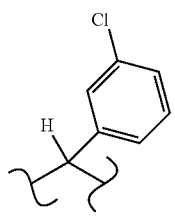 | 23 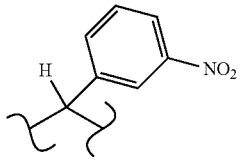 |
| 16 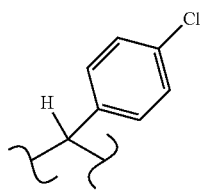 | 24 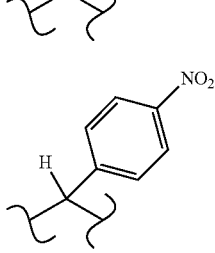 |
| 17 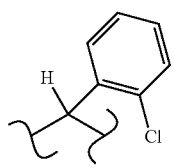 | 25 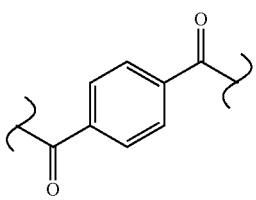 |
| 18 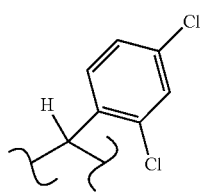 | 26 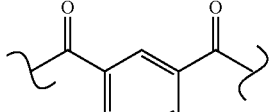 |
| 19 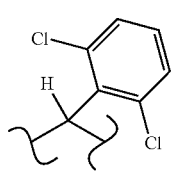 | 27 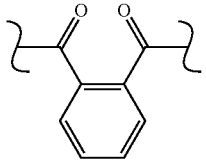 |
| | 28 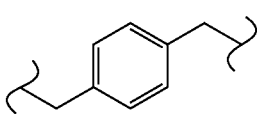 |

19
-continued

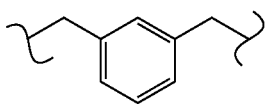

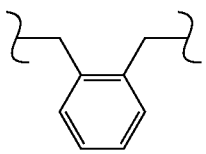

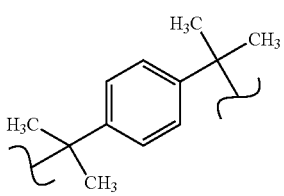

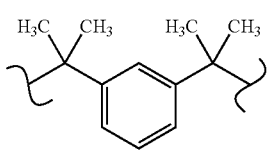

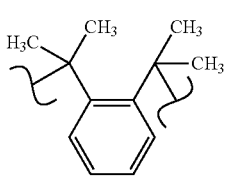

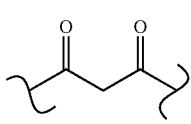

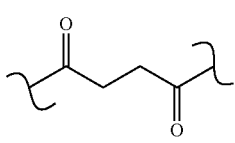

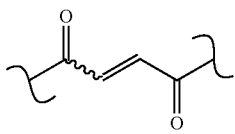

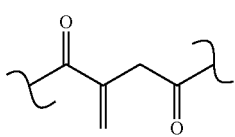

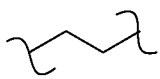

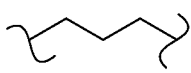

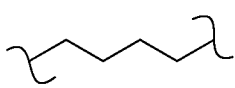

20
-continued

29

30

31

32

33

34

35

36

37

38

39

40

41 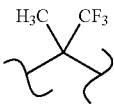

42 

43 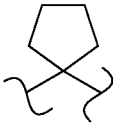

44 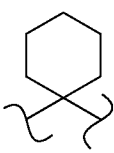

The structural elements 1 to 44 shown can in each case also carry the substituents referred to above and, if appropriate, have further, usually 1 or 2, ethylenic double bonds.

The structural element A can also be an aryl radical having 6 to 15, preferably 6 to 10, carbon atoms, specifically a phenylene, naphthylene or anthracenylene radical, or a heteroaryl radical as defined above having 2 to 15, preferably 3 to 10, carbon atoms.

The specified aryl and heteroaryl radicals may, if appropriate, in each case carry 1 to 5 substituents which are chosen from the group of abovedescribed substituents $C_1$-$C_6$-alkyl, $C_1$-$C_6$-perfluoroalkyl, $C_1$-$C_6$-alkoxy, $C_7$-$C_{12}$-aralkyl, halogen, —Si$R^{5d}R^{6d}$, $R^{7d}$, substituted or unsubstituted $C_6$-$C_{10}$-aryl, —N$R^{8d}R^{9d}$, S$R^{10d}$ and NO$_2$.

Furthermore, the structural element A can also be a functional group or a heteroatom which are chosen from the group —O—, —S—, —N($R^{11}$)—, —S(O)—, —C(O)—, —S(O)$_2$—, —P($R^{11}$)—, —($R^{11}$)P(O)—, —OP(O)O—, —OP(O)$_2$O— and —Si($R^{12}$)($R^{13}$)—, where the radicals $R^{11}$, $R^{12}$, $R^{13}$, independently of one another, are in each case an abovedescribed $C_1$-$C_6$-alkyl, $C_7$-$C_{12}$-aralkyl and/or substituted or unsubstituted $C_6$-$C_{10}$-aryl. Within this group, the structural element A is preferably —O—, —S—, —S(O)—, —S(O)$_2$— or —Si($R^{12}$)($R^{13}$)—.

Within the scope of the present invention, the term "ligand in free or complex-bound form" comprises both the free form of the ligand and all conceivable forms which can be converted into the free form under the process conditions. Examples thereof which may be mentioned are alkoxides of the ligand, which are converted to the free form of the ligand by basic hydrolysis.

Within the scope of the present invention, the expression "aqueous base" generally comprises aqueous solutions whose pH is greater than 7. In particular, these are aqueous solutions of alkali metal and alkaline earth metal hydroxides, specifically aqueous solutions of KOH and NaOH.

Within the scope of the present invention, the expression "aluminum-containing reaction product" is a reaction product which comprises at least one compound which comprises aluminum in ionic, covalent or complex-bound form. These are compounds of aluminum as result under the conditions of the method according to the invention from the compounds of the formula $(R^{14})_{3-p}AlH_p$ (II) or $MAlH_4$ (III), as defined below, used in the cyclization of citronellal.

Within the scope of the present invention, the expression "majority" should be understood as meaning a percentage fraction of the total amount of a compound present which is greater than 50%, preferably greater than 80% and particularly preferably greater than 90%.

Step a):

In step a) of the method according to the invention, the aluminum-containing reaction product from the production of isopulegol by cyclization of citronellal is subjected to distillative separation to give an isopulegol-enriched top product and an isopulegol-depleted bottom product.

In a specific embodiment, step a) uses a solvent with a higher boiling point than that of the isopulegol. In this way, undesired thermal stressing of the bottom contents can be avoided. In particular, the ligands of the formula (I) present therein are not in a form free from solvent while separating off the isopulegol. The higher-boiling solvent can be added to the aluminum-containing reaction product before and/or during distillative separation. Preference is given to using a higher-boiling solvent whose boiling point under the conditions of the distillation is above the boiling point of the isopulegol. Preferably, the boiling point of the introduced solvent under the conditions of the distillation is at least 5° C., preferably at least 10° C. and in particular at least 20° C., above the boiling point of the isopulegol.

Preferred higher-boiling solvents which have such a boiling point are, for example, hydrocarbons, such as phenylcyclohexane, benzyltoluene, dibenzyltoluene, 1-methylnaphthalene and tridecane, 1-decanol, 1,2-propylene carbonate, ethers, such as diethylene glycol dibutyl ether, tetraethylene glycol dimethyl ether and dibenzyl ether, and technical-grade mixtures of these solvents. Particular preference is given to mixtures which comprise phenylcyclohexane as main constituent.

When using at least one higher-boiling solvent, the isopulegol-depleted bottom product in step a) obtained is an organic phase comprising the higher-boiling solvent, the majority of the ligands of the formula (I) and, if appropriate, at least one aluminum-containing compound.

Preferably, distillative separation of isopulegeol in step a) takes place at a bottom temperature of preferably at most 250° C., preferably at most 150° C. and particularly preferably at most 100° C. The lower bottom temperature is usually uncritical and is generally at least 0° C., preferably at least 20° C. To maintain these maximum temperatures, the distillation can, if desired, be carried out under a suitable vacuum.

The pressure in step a) of the method according to the invention is, irrespective of the specific embodiment, generally in a range from 0.1 to 1500 mbar, preferably in a range from 1 to 500 mbar and particularly preferably in a range from 5 to 100 mbar.

Irrespective of the composition of the aluminum-containing reaction product from the cyclization of citronellal and of the use of a higher-boiling solvent, distillative separation of the isopulegol can take place continuously or batchwise, preferably continuously. In one suitable procedure, the higher-boiling solvent is added to the reaction product from the cyclization of citronellal before distillative separation and in the course of the distillation the amount of high-boiling solvent present in the bottom is subsequently kept constant.

For the distillative separation in step a), the customary devices known to the person skilled in the art can be used (see e.g. Sattler, Thermische Trennverfahren [Thermal separation methods], 2nd Edition 1995, Weinheim, p. 135ff; Perry's Chemical Engineers Handbook, 7th Edition 1997, New York, Section 13). These include distillation columns which may be provided with packings, internals etc. The distillation columns used can comprise separation-effective internals, such as separation trays, e.g. perforated trays, bubble-cap trays or valve trays, arranged packings, e.g. sheet-metal or fabric packings, or random beds of packings. The number of plates required in the column(s) used and the reflex ratio are essentially governed by the purity requirements and the relative boiling position of the constituents in the aluminum-containing reaction product from the production of isopulegol by cyclization of citronellal and of the higher-boiling solvent, where the person skilled in the art can ascertain the specific design and operating data by known methods. The distillative separation can, for example, take place in one or more distillation columns coupled together.

Likewise suitable for the distillative separation in step a) are customary evaporators, preferably evaporators with forced circulation, particularly preferably falling-film evaporators.

Depending on additional components which may, if appropriate, be present in the aluminum-containing reaction product from the cyclization of citronellal, the composition of the top product obtained during distillative separation may make it necessary to subject said product, if appropriate, to a further work-up step.

In a specific embodiment of the method according to the invention for working up an aluminum-containing reaction product from the production of isopulegol by cyclizing citronellal, the reaction product additionally comprises a lower-boiling solvent (iii).

Within the scope of the present invention, the expression "lower-boiling solvent (iii)" refers to the boiling point of the isopulegol. Of particular suitability here are those solvents or solvent mixtures which, under the conditions of the distillative separation, have a boiling point which is at least 5° C., preferably 10° C. and in particular 20° C. below that of the isopulegol under the respective conditions.

Within the scope of the present invention, preferred solvents with such a boiling point are inert organic solvents or mixtures thereof, such as, for example, aromatic solvents, e.g. toluene, ethylbenzene or xylene, halogenated solvents, e.g. dichloromethane, dichloroethane or chlorobenzene, aliphatic solvents, e.g. pentane, hexane or cyclohexane, ethers, e.g. tetrahydrofuran, diethyl ether, methyl tert-butyl ether, esters, e.g. ethyl acetate, or dimethylformamide (DMF), dimethyl sulfoxide (DMSO) and the like. Particular preference is given to toluene.

If the aluminum-containing reaction product to be worked up comprises such a lower-boiling solvent, then this is removed at least partially from the reaction product in a suitable embodiment prior to the distillative separation of the isopulegol. The lower-boiling solvent is likewise preferably separated off by distillation. Depending on the boiling point of the lower-boiling solvent, the customary abovementioned distillation devices can be used.

In a further suitable embodiment, distillative separation of the aluminum-containing reaction product in step a) takes place to give an isopulegol-enriched top product which at the same time comprises at least some, preferably the majority, of the lower-boiling solvent. In this case, the top product can be subjected to further separation, preferably likewise by distillation.

The separated-off lower-boiling solvent is advantageously returned to the cyclization of the citronellal by using it as solvent. In this way, the method according to the invention requires—apart from top-ups which are required as a result of unavoidable losses—just the single provision of an amount of the lower-boiling solvent.

In a specific embodiment of the method according to the invention for working up an aluminum-containing reaction product from the production of isopulegol by cyclizing citronellal, the reaction product additionally comprises an auxiliary (iv).

Within the scope of the present invention, the term "auxiliary (iv)" refers to compounds which are added during the cyclization of citronellal in order to suppress undesired secondary reactions. Preferably, the auxiliaries (iv) are chosen from organic acids, carboxylic anhydrides, aldehydes, ketones and vinyl ethers.

Specifically, the auxiliaries (iv) are chosen from acids, preferably organic acids. By way of example, organic acids which may be mentioned are: acetic acid, propionic acid, benzoic acid, toluenesulfonic acid, methanesulfonic acid, preferably acetic acid.

In a further specific embodiment of the present invention, the auxiliaries (iv) are chosen from carboxylic anhydrides, aldehydes, ketones and vinyl ethers.

The auxiliaries (iv) of said classes of substance can in each case be present individually or in the form of mixtures in the reaction product to be worked up. Preferred mixtures are those which consist of compounds of one class of substance. The reaction product particularly preferably comprises a single auxiliary.

Preferably, the auxiliaries (iv) present in the reaction product from the cyclization of citronellal are likewise at least partially removed and as far as possible returned to the cyclization of citronellal.

If the auxiliaries (iv) under the conditions of the distillation have a boiling point which is below or only slightly, i.e. less than 30° C., above the boiling point of the isopulegol, these can be largely recovered from the fully reacted mixture by distillation to the extent to which it was not, if appropriate, itself reacted. Depending on the boiling point of the auxiliary, the customary abovementioned distillation devices can be used.

If the auxiliaries (iv) have a boiling point under the conditions of the distillation which is significantly above, i.e. at least 30° C., above the boiling point of the isopulegol, these remain in the bottom product and are, if appropriate, removed in step b) of the method according to the invention if their physical properties allow this.

In a further suitable embodiment, distillative separation of the reaction product in step a) takes place to give an isopulegol-enriched top product which at the same time comprises at least some, preferably the majority, of the auxiliary (iv). If appropriate, this main product can comprise a lower-boiling solvent, as explained above. In this case, the top product can be subjected to further separation, preferably likewise by distillation. The separated-off auxiliary (iv) is, if appropriate together with the lower-boiling solvent, advantageously returned to the cyclization of the citronellal, where it is used, for example, for suppressing undesired secondary reactions. In this way, the method according to the invention requires—apart from top-ups which are required as a result of unavoidable losses—just a single provision of an amount of the auxiliary (iv).

The separating off of isopulegol, the introduction of the higher-boiling solvent and, if appropriate, the separating off of low-boiling components, i.e. the separating off of any solvents present and volatile auxiliaries from the cyclization of citronellal, can be combined in various ways:

In one suitable embodiment, a so-called dividing wall column is used for the distillation, i.e. feed point and a side take-off are located on opposite sides of a dividing wall which extends along a section of the longitudinal expansion of the column. Such distillation columns which comprise a dividing wall are known per se to the person skilled in the art. If side take-off and feed are in the region of the dividing wall, a connection analogous to a Brugma or Petlyuk connection arises. Such distillations using dividing wall columns are described in DE-A-33 02 525 and EP-A-0 804 951, to the entire scope of which reference is hereby made. In this case, a fraction enriched with low-boiling components can be removed as top product, and a stream comprising the majority of isopulegol can be removed as side take-off, for example. The higher-boiling solvent is introduced below the feed point, preferably into the bottom of the column or just above the bottom. A solution of the majority of the ligand of the formula (I) in the higher-boiling solvent is produced as bottom product.

In an alternative embodiment, coupled columns are used for the distillation. This embodiment may be advantageous if the reaction product of the cyclization of citronellal comprises a solvent and/or a volatile auxiliary, as explained in more detail below.

In this case, mixtures of isopulegol and lower- or slightly higher-boiling solvents and/or auxiliary (iv) can form the top product of the first column and in the second column be subjected to separation to give a stream comprising at least the majority of the isopulegol and an isopulegol-depleted stream comprising the lower-boiling solvents and/or auxiliaries of the cyclization.

Streams which comprise lower-boiling solvents (iii) and auxiliary (iv) of the cyclization can usually be returned to the cyclization without further separation.

The ligands of the formula (I) are produced, if appropriate in the form of their complexes or other derivatives, as bottom product of the first column.

Step b):

In step b) of the method according to the invention, the isopulegol-depleted bottom product is brought into close contact with an aqueous base to give an aluminum-containing aqueous phase and an organic phase comprising the majority of the ligands of the formula (I). Preferred aqueous bases are given above.

Besides the ligand of the formula (I) in free or complex-bound form, the isopulegol-depleted bottom product obtained in step a) can comprise at least one further low-volatile component. These include, for example, higher-boiling solvents added in step a), the reaction products of the aluminum-containing compounds used for the cyclization of citronellal to isopulegol, and, if appropriate, auxiliaries (iv) not separated off in step a). Since aluminum-containing components and/or the auxiliaries (iv) accumulate particularly in the case of a continuous method and have an adverse effect especially on the yield and purity of the separation in step c), it is advantageous to remove these compounds as completely as possible. This applies specifically to the aluminum-containing compounds.

The bringing into contact in step b) preferably takes place by extraction. The number of extraction stages is preferably in a range from 1 to 20 stages.

The extractants used are the abovementioned aqueous bases. These expressions are therefore used synonymously within the scope of the present invention.

For the extraction, the isopulegol-depleted bottom product from step a) is brought into close contact with an aqueous base. Separation of the phases gives a phase comprising the majority of the ligand of the formula (I) and an aqueous phase enriched in aluminum-containing compounds. The aqueous phase is then removed. The bringing into contact can take place continuously or batchwise.

For the batchwise procedure the isopulegol-depleted bottom product from step a) and the aqueous extractant are brought into contact with mechanical agitation, e.g. by stirring, in a suitable vessel, the mixture is left to stand for phase separation and one of the phases is removed by expediently removing the denser phase at the bottom of the vessel.

A plurality of batchwise separation operations can be carried out successively in a cascade-like manner, in which case the phase separated off from the aqueous phase and comprising the majority of the ligand of the formula (I) is in each case brought into contact with a fresh portion of the aqueous extractant and/or the aqueous extractant is passed countercurrently.

The extraction preferably takes place continuously. For the continuous extraction procedure, the aqueous extractant and the stream of isopulegol-depleted bottom product from step a) are introduced continuously into suitable apparatuses in a manner analogous to the batchwise variant. At the same time, a discharge of the phase comprising the majority of the ligand of the formula (I) and a discharge of the aqueous phase enriched in aluminum-containing compounds are continuously removed from the apparatus in which the separation of the phases takes place.

The extraction takes place at least in one stage, e.g. in a mixer-separator combination. Suitable mixers are either dynamic or static mixers. Extraction in a plurality of stages takes place, for example, in a plurality of mixer-separators or extraction columns.

In one suitable embodiment, at least one coalescing device is used to improve phase separation. This is preferably chosen from coalescing filters, electrocoalescers and combinations thereof. When using mixer-separator devices for the extraction, the use of coalescing filters, such as candle filters or sand filters, has proven advantageous for improving phase separation. The filter can be installed here directly after the mixer (stirred container) and/or in the organic run-off from the separator. Also preferred for improving phase separation is the use of electrocoalescers. These have proven useful for separating off aqueous foreign phases of up to 5% by mass. The use of coalescing devices is also advantageously suitable in the method according to the invention for separating off finely dispersed aqueous phase from the organic discharge of an extraction column comprising the majority of the ligand of the formula (I).

In one suitable embodiment, the extraction takes place in at least one mixer-separator combination for the extraction of aluminum-containing components from the isopulegol-depleted bottom product from step a). The use of a further mixer-separator combination is particularly advantageous for subsequently reextracting and thus returning to the process fractions of the ligand of the formula (I) or, if appropriate, of the higher-boiling solvent which, if appropriate, with the aluminum-containing compounds to be separated off, partially pass into the extractant.

The extraction is preferably carried out continuously in two serially connected heatable mixers, where the aqueous base is passed into the first stirred apparatus with the isopulegol-depleted bottom product from step a) and the resulting mixture is transferred to a second stirred apparatus. From this second stirred apparatus, the mixture is then fed to a separator where phase separation into a relatively heavily aqueous phase and a relatively light organic phase takes place. As a result of this cascading of the mixers, a more complete hydrolysis and/or extraction of the aluminum-containing compounds is achieved. The stirred apparatuses used are containers (stirred-tank reactor) equipped with stirrers and heatable with steam and/or warm water that are known to the person skilled in the art. The phase separation container used is advantageously a horizontally installed, likewise heatable container which is heated such that no solids can separate out from the individual phases.

Under certain circumstances, it may be advantageous to subject the organic phase comprising the majority of ligands of the formula (I) to a drying step before separating off the ligand in step c) or after separating it off. Suitable drying methods are the customary ones known to the person skilled in the art, in particular the adsorption to dehydrating agents, e.g. using a zeolitic molecular sieve.

In an alternative embodiment of the method according to the invention, after bringing the isopulegol-depleted bottom product into contact with the aqueous base, the water is completely or at least partially removed by distillation.

In order to prevent the ligand of the formula (I) from separating off prematurely, specifically by crystallization, at no point during step b) should the concentration of the ligand in the organic phase exceed its solubility. This can be carried out through appropriate choice of the temperature and/or the amount and type of added solvents, if appropriate.

Consequently, in a preferred embodiment of the method according to the invention, a discharge of the heated bottom product from step a) is brought into close contact with a heated aqueous base.

Within the scope of the present invention, the expression "heated" refers to a temperature above room temperature and below the respective boiling point temperatures of the aqueous or organic solutions under the reaction conditions in question. In particular, heated refers to a temperature in the range from 25° C. to 150° C., specifically in the range from 70° C. to 100° C.

Depending on the auxiliaries used, if appropriate, in the cyclization of citronellal, the isopulegol-depleted bottom product can, if appropriate, comprise further components not separated off in step a). These are preferably separated off in step b). In this case, the aqueous phase obtained can be subjected to a suitable separation process in order to recover these components, e.g. an auxiliary (iv).

Step c):

In step c) of the method according to the invention, the above-described ligand of the formula (I) from the organic phase containing the majority of the ligand obtained in step b) is separated off from the organic phase by means of the above-described method for separating off a substance from a solution. As described above, in this method electromagnetic radiation is radiated into the solution and the intensity of the electromagnetic radiation that has been scattered by the crystals located in the solution is detected. In this case, these are crystals of the ligand. The detected intensity is then compared with the desired intensity and the temperature of the solution is regulated depending on the difference between the detected intensity and the desired intensity in such a way that this difference is reduced. If ultimately the amount of difference between the detected intensity and the desired intensity is less than the limiting value, the crystallization method, in particular the cooling crystallization, is started. The obtained crystals of the ligand are then separated off.

In the method according to the invention, in particular the following aluminum phenolate catalyst with a sterically very demanding ligand is used:

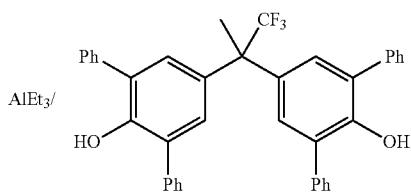 [SMILES: "AlEt3/" ; CC(c1cc(-c2ccccc2)c(O)c(-c2ccccc2)c1)(c1cc(-c2ccccc2)c(O)c(-c2ccccc2)c1)C(F)(F)F]

During the recovery of this ligand by cooling crystallization from a solution in phenylcyclohexane, the crystal formation takes place only comparatively slowly on account of the complex structure of the molecule. The supercoolability of the crystallization solution can be up to 50 K for this ligand. It is therefore particularly difficult to arrive at a crystallization of the ligand in a readily filterable crystal size and morphology. A measure of this is the attainment of a filter resistance, which is $5*10^{13}$ mPasm$^{-2}$ for a readily filterable product. If the solution is inoculated too much or too little, the filter resistance changes by more than one order of magnitude to more than $10^{15}$ mPasm$^{-2}$.

If the above-described ligand is to be separated off from the solution, the solution or some of the solution is brought in a crystallization vessel preferably to a temperature which is lower than 95° C., in particular lower than 90° C. The temperature is then increased until the detected intensity of the scattered electromagnetic radiation has come close as described to the desired intensity. The temperature for the cooling crystallization is then reduced again. The cooling rate at the start is in a range from 1 K/h to 5 K/h.

By virtue of the method according to the invention, a precisely measured amount of seed crystal is provided at the start of the crystallization method. This means that despite the complex molecular structure of the ligand, it can be recovered in a short time with high yield.

In this crystallization method, besides the described cooling crystallization method, it may moreover also be an evaporative crystallization method, a vacuum crystallization method and a method which uses crystallizing chutes or jet crystallizers.

In general, the crystallization takes place at a temperature in the range from −50° C. to 150° C., preferably in the range from 0° C. to 120° C. and specifically in a range from 30° C. to 110° C.

The crystalline ligand of the formula (I) can be isolated from the solution, for example, by filtration, floatation, centrifugation or sieving.

The ligand of the formula (I) retained in this way can, if appropriate, be dried by suitable drying methods. Methods for this are known to the person skilled in the art. For example, for the technical configuration of the method, customary roller dryers, disk dryers, chamber dryers, fluidized-bed dryers or radiation dryers may be suitable.

The organic phase depleted in ligand of the formula (I) can again be added to the process before or during step a).

In a preferred embodiment of the method for working up a reaction product from the production of isopulegol, the ligand of the formula (I) is chosen from bis(diarylphenol) ligands of the formula (I.a)

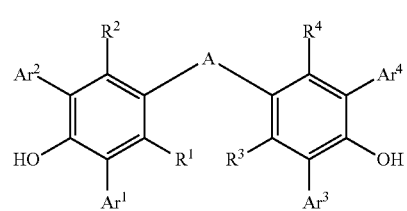

where $Ar^1$, $Ar^2$, $Ar^3$, $Ar^4$, $R^1$, $R^2$, $R^3$, $R^4$ and A have the meanings given above.

The ligands of the formula (Ia) likewise have two phenol systems which in each case are substituted in both ortho positions relative to the phenolic hydroxy group by aromatics or heteroaromatics ($Ar^1$ to $Ar^4$) and are joined together via a structural element A and, if appropriate, can also carry further substituents ($R^1$ to $R^4$), the structural element A being joined to the two phenol systems in each case in the para position relative to the phenolic hydroxy group. Here, the radicals $Ar^1$, $Ar^2$, $Ar^3$, $Ar^4$, the radicals $R^1$, $R^2$, $R^3$, $R^4$ and the structural element A can have the same meanings as specified above for formula (I).

According to the invention, particularly preferred ligands are those in which the aryl radicals $Ar^1$, $Ar^2$, $Ar^3$ and $Ar^4$ are identical and have the preferred meanings given above for formula (I). Particularly preferred aryl radicals $Ar^1$ to $Ar^4$ are phenyl, naphthyl, 4-fluorophenyl, 4-chlorophenyl, 3-chlorophenyl, 3,5-dichlorophenyl, 4-methylphenyl, 3-trifluoromethylphenyl, 4-trifluoromethylphenyl, very particularly preferably phenyl.

In the ligands of the formula (I.a) preferred according to the invention, the radicals $R^1$, $R^2$, $R^3$, $R^4$ are identical or different, preferably identical, and are preferably: hydrogen, halogen, in particular fluorine or chlorine, methyl, trifluoromethyl, isopropyl, tert-butyl, phenyl, nitro.

The structural element A in formula (I.a) has the meanings given above for formula (I). Preferred structural elements A in formula (I.a) are in particular also the structural elements 1 to 44 which may be substituted in the specified manner.

Particularly preferred ligands are those of the formulae (I.a) to (I.a$_3$), where the specified radicals $Ar^1$ to $Ar^4$, $R^1$ to $R^4$ and $R^{15}$ to $R^{18}$ preferably have the meanings listed by way of example in the table:

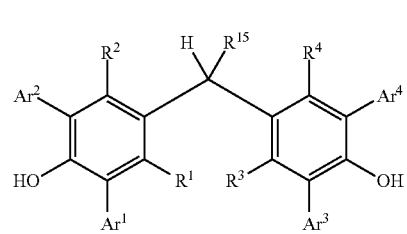

TABLE 1

| Compound | $Ar^1$ | $Ar^2$ | $Ar^3$ | $Ar^4$ | $R^1$ | $R^2$ | $R^3$ | $R^4$ | $R^{15}$ |
|---|---|---|---|---|---|---|---|---|---|
| Ia$_1$-1 | Ph | Ph | Ph | Ph | H | H | H | H | H |
| Ia$_1$-2 | Ph | Ph | Ph | Ph | H | H | H | H | CH$_3$ |
| Ia$_1$-3 | Ph | Ph | Ph | Ph | H | H | H | H | Ph |
| Ia$_1$-4 | Ph | Ph | Ph | Ph | H | H | H | H | CF$_3$ |
| Ia$_1$-5 | Ph | Ph | Ph | Ph | H | H | H | H | CCl$_3$ |
| Ia$_1$-6 | Ph | Ph | Ph | Ph | H | H | H | H | 4-Cl—Ph |

TABLE 1-continued

| Compound | Ar¹ | Ar² | Ar³ | Ar⁴ | R¹ | R² | R³ | R⁴ | R¹⁵ |
|---|---|---|---|---|---|---|---|---|---|
| Ia₁-7 | Ph | Ph | Ph | Ph | H | H | H | H | CH₂CH₃ |
| Ia₁-8 | Ph | Ph | Ph | Ph | H | H | H | H | 3-NO₂—Ph |
| Ia₁-9 | Ph | Ph | Ph | Ph | H | H | H | H | (CH₃C(O)CH(—)—) |

TABLE 2

| Compound | Ar¹ | Ar² | Ar³ | Ar⁴ | R¹ | R² | R³ | R⁴ | R¹⁶ | R¹⁷ |
|---|---|---|---|---|---|---|---|---|---|---|
| Ia₂-1 | Ph | Ph | Ph | Ph | H | H | H | H | CF₃ | CF₃ |
| Ia₂-2 | Ph | Ph | Ph | Ph | H | H | H | H | CCl₃ | CCl₃ |
| Ia₂-3 | Ph | Ph | Ph | Ph | H | H | H | H | CH₃ | CF₃ |
| Ia₂-4 | Ph | Ph | Ph | Ph | H | H | H | H | CH₃ | CCl₃ |
| Ia₂-5 | Ph | Ph | Ph | Ph | H | H | H | H | CH₂CH₃ | CF₃ |
| Ia₂-6 | Ph | Ph | Ph | Ph | H | H | H | H | CH₃ | CH₃ |
| Ia₂-7 | Ph | Ph | Ph | Ph | H | H | H | H | CH₃ | C(O)OCH₃ |
| Ia₂-8 | Ph | Ph | Ph | Ph | H | H | H | H | CH₃ | C(O)OC₂H₅ |
| Ia₂-9 | Ph | Ph | Ph | Ph | H | H | H | H | —(CH₂)₃— | |
| Ia₂-10 | Ph | Ph | Ph | Ph | H | H | H | H | —(CH₂)₄— | |
| Ia₂-11 | Ph | Ph | Ph | Ph | H | H | H | H | —(CH₂)₅— | |

(I.a₂)

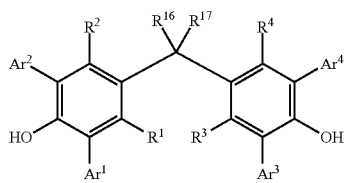

(I.a₃)

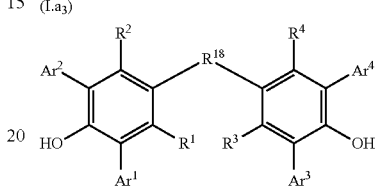

TABLE 3

| Compound | Ar¹ | Ar² | Ar³ | Ar⁴ | R¹ | R² | R³ | R⁴ | R¹⁸ |
|---|---|---|---|---|---|---|---|---|---|
| Ia₃-1 | Ph | Ph | Ph | Ph | H | H | H | H | —(CH₂)₂— |
| Ia₃-2 | Ph | Ph | Ph | Ph | H | H | H | H | 1,4-C₆H₄(C(O)—)₂ |
| Ia₃-3 | Ph | Ph | Ph | Ph | H | H | H | H | 1,2-C₆H₄(C(O)—)₂ |
| Ia₃-4 | Ph | Ph | Ph | Ph | H | H | H | H | —C(O)CH₂CH₂C(O)— |
| Ia₃-5 | Ph | Ph | Ph | Ph | H | H | H | H | —C(O)CH=CHC(O)— |
| Ia₃-6 | Ph | Ph | Ph | Ph | H | H | H | H | 1,4-C₆H₄(C(CH₃)₂—)₂ |

TABLE 3-continued

| Compound | Ar¹ | Ar² | Ar³ | Ar⁴ | R¹ | R² | R³ | R⁴ | R¹⁸ |
|---|---|---|---|---|---|---|---|---|---|
| Ia₃-7 | Ph | Ph | Ph | Ph | H | H | H | H | 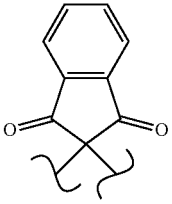 |

Here, in Tables 1-3, Ph is a phenyl radical and C(O) is a carbonyl group within the scope of the present invention. In general, the radicals $R^{15}$, $R^{16}$ and $R^{17}$ can, independently of one another, be an abovedefined $C_1$-$C_6$-alkyl, $C_1$-$C_{10}$-acyl, $C_1$-$C_{10}$-carboxyl or $C_6$-$C_{10}$-aryl, where the specified radicals can carry one or more identical or different halogen and/or $NO_2$ substituents and where the radicals $R^{16}$ and $R^{17}$ can together also form a cyclic structural element, preferably an alkylene bridge.

In a preferred embodiment of the above-described method for separating off a substance from a solution, the substance is a ligand of the formula (I) selected from bis(diarylphenol) ligands of the above formula (I.a). Particularly preferred ligands are those of the above formulae (I.a₁) to (I.a₃), the specified radicals $Ar^1$ to $Ar^4$, $R^1$ to $R^4$ and $R^{15}$ to $R^{18}$ preferably being attributed to the meanings listed above in the table by way of example.

The present invention further provides a method for producing isopulegol of the formula (IV)

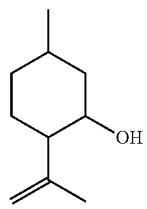 (IV)

comprising

α) the cyclization of citronellal of the formula (V)

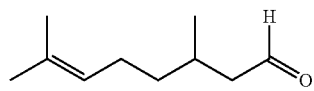 (V)

in the presence of a catalyst which is obtainable by reacting a bis(diarylphenol) ligand of the formula (I) as defined in claims 1 and/or 10,
with an aluminum compound of the formula (II),

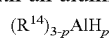 (II)

where
Al is aluminum,
$R^{14}$ is a branched or unbranched alkyl radical having 1 to 5 carbon atoms and
p is 0 or an integer from 1 to 3,
and/or
with an aluminum compound of the formula (III), $MAlH_4$ (III)

where
Al is aluminum and
M is lithium, sodium or potassium,

β) the recovery of the bis(diarylphenol) ligand of the formula (I) after the reaction has taken place by
a) subjecting the aluminum-containing reaction product obtained in step a) to distillative separation to obtain an isopulegol-enriched top product and an isopulegol-depleted bottom product,
b) bringing the isopulegol-depleted bottom product into close contact with an aqueous base to give an aluminum-containing aqueous phase and an organic phase comprising the majority of the ligands of the formula (I) and
c) separating off the ligand of the formula (I) from the organic phase.

The separating off of the ligand of the formula (I) takes place here by crystallization, and specifically in the course of the above-described method for separating off a substance from a solution.

With regard to the preferred embodiments of the method according to the invention for working up a reaction product from the production of isopulegol by cyclization of citronellal, and for the preferred ligands of the formula (I), reference is made to the abovementioned preferred embodiments in their entirety.

The bis(diarylphenol) ligands of the formulae (I) and (I.a) which can be used for producing the bis(diarylphenoxy) aluminum compounds used according to the invention can be prepared easily by methods known per se to the person skilled in the art.

Compounds of structure type (I.a₁) are obtained, for example, by reacting the corresponding bis-ortho-arylphenols with an aldehyde $R^{15}$CHO in the presence of a Lewis acid, for example $AlCl_3$, as described, inter alia, by Z. Y. Wang, A. S. Hay in Synthesis 1989, 471-472 or in U.S. Pat. No. 3,739,035. Ligands of structure type (I.a₂) are, for example, accessible by reacting the corresponding bis-ortho-arylphenols with a suitable ketone of the formula $R^{16}$C(O)$R^{17}$, as described, for example, in U.S. Pat. No. 3,739,035. Ligands of structure type (I.a₃) are, for example, accessible by Friedel-Crafts acylation of the corresponding phenols or O-protected phenols with dicarboxylic acid chlorides, as described, for example, by F. F. Blicke et al. in J. Am. Chem. Soc. 1938, 60, 2283-2285; CH 350461 or by G. Maier et al. in Chem. Ber. 1985, 118, 704-721. Another way of producing ligands of structure type (Ia₃) also consists in the Friedel-Crafts alkylation of the corresponding phenols with tertiary diols, as described, for example, in DE-A 25 34 558, or with dihalides, as described, for example, by J. Zavada, in Collect. Czech. Chem. Commun., 1976, 41, 1777-1790.

The bis(diarylphenoxy)aluminum compounds used according to the invention are obtained, for example, by reacting the abovedescribed bis(diarylphenol) ligands of the formulae (I) or (I.a) with an aluminum compound of the formula (II)

$(R^{14})_{3-p}AlH_p$ (II),

Here, $R^{14}$ is a branched or unbranched alkyl radical having 1 to 5 carbon atoms, such as, for example, methyl, ethyl, propyl, isopropyl, butyl, isobutyl, pentyl, isopentyl or neopentyl. The index p is 0 or an integer from 1 to 3. Preferably, the index p is 1 or 0, particularly preferably 0. Preferred compounds of the formula (II) are, for example, trimethylaluminum, triethylaluminum, diisobutylaluminum hydride, particularly preferably trimethylaluminum and triethylaluminum.

Alternatively to this, the bis(diarylphenoxy)aluminum compounds used according to the invention are also obtained by reacting the abovedescribed bis(diarylphenol) ligands of the formulae (I) or (Ia) with an aluminum compound of the formula (III)

$MAlH_4$ (III), where M is lithium, sodium or potassium. Consequently, of suitability for producing the bis(diarylphenoxy)aluminum compounds used according to the invention by reacting the abovedescribed bis(diarylphenol) ligands of the formulae (I) or (I.a) are also lithium aluminum hydride, sodium aluminum hydride and potassium aluminum hydride, and mixtures thereof. Moreover, mixtures of the specified compounds of the formulae (II) and (III) are also suitable for producing bis(diarylphenoxy)aluminum compounds used according to the invention by reaction with the abovedescribed bis(diarylphenol) ligands of the formulae (I) or (I.a).

The reaction is advantageously carried out so that one of the abovedescribed bis(diarylphenol) ligands of the formulae (I) or (Ia) is brought into contact with a compound of the formula (II) or (III). The reaction is advantageously carried out in an inert organic solvent, such as, for example, toluene, cyclohexane, dichloromethane, xylene, ethylbenzene, chlorobenzene, tetrahydrofuran, diethyl ether, methyl tert-butyl ether, ethyl acetate, pentane, hexane, dichloroethane, dimethylformamide (DMF), dimethyl sulfoxide (DMSO) and more besides, the use of predried or anhydrous solvents being regarded as particularly advantageous. The reaction is usually carried out at temperatures in the range from about −100° C. to about 100° C., preferably at about −50° C. to about 50° C., particularly preferably at about −30° C. to about 30° C.

During the production of the bis(diarylphenoxy)aluminum compounds according to the invention, the phenolic hydroxy groups of the bis(diarylphenol) ligands of the formulae (I) or (I.a) used react with the compound or compounds of the formulae (II) and (III). Theoretically, each aluminum atom can react with 1 to 3 phenolic hydroxy groups. On account of the steric properties or requirements of the bis(diarylphenol) ligands of the formulae (I) or (I.a) used, this results in the formation of higher molecular weight structures such as linear structures or networks.

Here, the molar ratio of the bis(diarylphenol) ligands of the formulae (I) or (I.a) used to the compounds of the formula (II) and/or (III) used is advantageously chosen such that the amount of incompletely reacted compounds of the formulae (II) and/or (III) is as low as possible. Preferably, the specified ratio is chosen so that, after the bis(diarylphenol) ligands of the formulae (I) or (I.a) have been brought into contact with the compound or the compounds of the formulae (II) and (III), any unreacted compound of the formula (II) and/or (III) is no longer present. Taking into consideration the cost aspect, it is advisable to keep the excess of the ligands of the formulae (I) or (I.a) used low. Particular preference is given to using bis(diarylphenol) ligands of the formulae (I) or (I.a) and the compounds of the formulae (II) and/or (III) in a molar ratio of from about 4:1 to about 1:1, very particularly preferably from about 3:1 to about 1.5:1 and most preferably in the molar ratio of about 1.5:1.

Within the scope of a preferred embodiment of the present invention, the production of the bis(diarylphenoxy)aluminum compounds used according to the invention involves initially introducing, depending on the solubility, an about 0.001 to about 1 molar solution of the chosen ligand of the formula (I) or (I.a) into a suitable organic solvent, for example toluene, at a temperature of from about −10 to about 30° C., and adding an aluminum compound of the formula (II) and/or (III), preferably in the form of a solution, for example a solution of trimethyl- or triethylaluminum in toluene.

The reaction between the ligands of the formula (I) or (I.a) used and the aluminum compounds of the formulae (II) and/or (III) usually takes place rapidly and is mostly complete after about 10 min to about 2 h, often after about 1 h, depending on the reaction conditions chosen. When using more unreactive reactants, it may be advantageous to temporarily increase the temperature of the reaction mixture.

Depending on the reaction conditions chosen, in particular with regard to the solubility of the ligands of the formula (I) or (I.a) to be reacted and of the aluminum compound of the formula (II) and/or (III) in the chosen solvents, the concentrations and the reaction temperatures, the bis(diarylphenoxy)aluminum compounds according to the invention are obtained in the form of a solid, a suspension or a solution in the solvent or solvent mixture used. The bis(diarylphenoxy)aluminum compounds used according to the invention obtained in this way can be further used in the form obtained in each case or can be separated off and freed from the solvents used.

Isolation can take place here by methods which appear to be advantageous and are known to the person skilled in the art. Preferably, the isolation, storage and further treatment of the bis(diarylphenoxy)aluminum compounds used according to the invention are carried out with extensive exclusion of oxygen and moisture.

To carry out the method according to the invention for producing isopulegol, the procedure advantageously involves firstly preparing a solution of the bis(diarylphenoxy)aluminum compounds used according to the invention in a suitable solvent, as described above. The racemic or nonracemic citronellal to be cyclized is then added according to the invention to this solution. The citronellal can here be added as it is or in the form of a solution, advantageously in one of the abovementioned suitable solvents. Within the scope of a preferred embodiment of the method according to the invention, a solution of the chosen ligand of the formulae (I) or (I.a) in toluene is firstly prepared and then, advantageously with stirring, the chosen aluminum compound of the formula (II) and/or (III), preferably trimethylaluminum or triethylaluminum in toluenic solution, is added.

A suitable starting material for carrying out the cyclization method according to the invention is citronellal, which can be produced by any method. Preference is given to using citronellal which has a purity of about 90 to about 99.9% by weight, particularly preferably from about 95 to about 99.9% by weight.

The addition of the citronellal to be cyclized advantageously takes place at temperatures in the range from about −40° C. to about 40° C., preferably in the range from about −20° C. to about 20° C. For this, the prepared solution of the bis(diarylphenoxy)aluminum compound used according to the invention is advantageously cooled to a temperature in this range, e.g. to a temperature in the range from −10° C. to 10° C., and prechilled citronellal or a prechilled solution of citronellal is added.

The addition of the citronellal or of the solution thereof can be undertaken such that either the whole amount is added at once or it is added in portions or else continuously to the prepared catalyst solution. Suitable solvents in turn are the abovementioned solvents, in particular toluene. Preferably, the citronellal to be cyclized is used as it is, i.e. without the further addition of solvents. When using a solvent, the total amount of solvent (for catalyst production and for carrying out the cyclization reaction) is advantageously chosen so that the volume-based ratio of citronellal to be reacted to solvent is about 2:1 to about 1:20, preferably from about 1.5:1 to about 1:10.

The quantitative ratio between the citronellal to be reacted and the amount of bis(diarylphenoxy)aluminum compound employed according to the invention used is determined by the amount of compounds of the formula (I) or (I.a) and of the formula (II) and/or (III) used for producing the same, i.e. by the quantitative ratio of ligand used to aluminum compound of the formula (II) and/or (III) used.

According to the invention, the amount of citronellal to be reacted relative to the amount of aluminum compound of the formula (II) and/or (III) used is chosen such that the molar ratio is about 5:1 to about 1000:1, preferably about 10:1 to about 500:1, particularly preferably about 50:1 to about 200:1.

Irrespective of this, the ratio between ligand of the formula (I) or (I.a) used and the aluminum compound of the formula (II) and/or (III) used can be varied within the limits specified above for producing the bis(diarylphenoxy)aluminum compound according to the invention.

The cyclization of citronellal to isopulegol generally takes place rapidly, depending on the choice of reactants and reaction conditions, and is usually largely complete after about 0.5 to about 10 h, often after about 5 h. Reaction progress can be easily monitored by methods known per se to the person skilled in the art, for example by chromatographic, specifically gas chromatographic, methods or else HPLC methods, Within the scope of a preferred embodiment of the method according to the invention, the cyclization of citronellal to isopulegol is carried out in the presence of an auxiliary (iv), for example an acid, preferably an organic acid. By way of example, organic acids which can be used advantageously are: acetic acid, propionic acid, benzoic acid, toluenesulfonic acid, methanesulfonic acid, preferably acetic acid. The specified acids are advantageously used in an amount of from about 0.5 to about 10% by weight, based on the amount of citronellal to be reacted. Advantageously, they are added to the reaction mixture together with the citronellal, e.g. in the form of a mixture.

In a particularly preferred embodiment, the method according to the invention for producing isopulegol by cyclizing citronellal is carried out in the presence of at least one auxiliary (iv) which is chosen from carboxylic anhydrides, aldehydes, ketones and vinyl ethers.

The auxiliaries (iv) of the specified classes of substance can in each case be used individually or in the form of mixtures with one another. In the case of mixtures, preference is given to using those which consist of compounds of one class of substance. Particular preference is given to using individual compounds. By using the specified compounds as described below, it is generally possible to largely suppress the formation of undesired by-products.

Within the scope of a preferred embodiment, the cyclization of citronellal is carried out in the presence of a carboxylic anhydride of the formula (VI)

where the radicals $R^{20}$ and $R^{20'}$ may be identical or different, preferably identical, and are a branched or unbranched $C_1$-$C_{12}$-alkyl radical or $C_7$-$C_{12}$-aralkyl radical or a $C_6$-$C_{10}$-aryl radical, where the specified radicals may in each case have one or more, generally 1 to about 3, identical or different substituents chosen from the group $OR^{10e}$, $SR^{10f}NR^{8e}R^{9e}$ and halogen and where $R^{20}$ and $R^{20'}$ can together also form a 5- to 8-membered ring which can have one or more ethylenic double bonds and one or more identical or different heteroatoms chosen from the group O, S and $NR^{11b}$ and where $R^{10e}$, $R^{10f}$, $R^{8e}$, $R^{9e}$ and $R^{11b}$ can have the meanings given above for $R^{11}$.

Within the scope of a further preferred embodiment, the cyclization of citronellal is carried out in the presence of an aldehyde of the formula (VII)

where the radical $R^{21}$ is a branched or unbranched $C_1$-$C_{12}$-alkyl radical or $C_7$-$C_{12}$-aralkyl radical or a $C_6$-$C_{10}$-aryl radical, where the specified radicals can in each case have one or more, preferably 1 to 3, identical or different substituents chosen from the group $OR^{10e}$, $SR^{10f}NR^{8e}R^{9e}$ and halogen, where $R^{10e}$, $R^{10f}$, $R^{8e}$ and $R^{9e}$ can have the meanings given above for $R^{11}$.

Within the scope of a further preferred embodiment, cyclization of citronellal is carried out in the presence of a ketone of the formula (VIII) (VIII)

where the radicals $R^{22}$ and $R^{23}$ may in each case be identical or different and are a branched or unbranched $C_1$-$C_{12}$-alkyl radical or $C_7$-$C_{12}$-aralkyl radical or a $C_6$-$C_{10}$-aryl radical or a $C_1$-$C_6$-alkoxycarbonyl radical, where the specified radicals can in each case have one or more, preferably 1 to 3, identical or different substituents chosen from the group $OR^{10e}$, $SR^{10f}NR^{8e}R^{9e}$ and halogen, and where $R^{22}$ and $R^{23}$ can together also form a 5- to 8-membered ring which can have one or more ethylenic double bonds and one or more identical or different heteroatoms chosen from the group O, S, $NR^{11b}$ and where $R^{10e}$, $R^{10f}$, $R^{8e}$, $R^{9e}$ and $R^{11b}$ can have the meanings given above for $R^{11}$.

As an alternative to the abovementioned carbonyl compounds, it is also possible to use vinyl ethers of the general formula (IX)

(IX)

within the scope of the method according to the invention, where the radicals $R^{24}$, $R^{25}$, $R^{26}$ and $R^{27}$, independently of one another, may in each case be identical or different and are a branched or unbranched $C_1$-$C_{12}$-alkyl radical or $C_7$-$C_{12}$-aralkyl radical or a $C_6$-$C_{10}$-aryl radical, where the specified radicals can in each case have one or more, preferably 1 to 3, identical or different substituents chosen from oxo, $OR^{10e}$, $SR^{10f}$ $NR^{8e}R^{9e}$ and halogen and where $R^{25}$ and $R^{26}$ can together also form a 5- to 8-membered ring which can have one or more ethylenic double bonds and one or more, usually 1 or 2, identical or different heteroatoms chosen from the group O, S, $NR^{11b}$ and where $R^{10e}$, $R^{10f}$, $R^{8e}$, $R^{9e}$ and $R^{11b}$ can have the meanings given above for $R^{11}$.

$C_1$-$C_{12}$-Alkyl here is $C_1$-$C_6$-alkyl as described above and, moreover, for example heptyl, octyl, nonyl, decyl, undecyl or dodecyl. In the cases where two alkyl radicals together form a ring, alkyl radicals are also understood as meaning alkylenyl radicals. $C_7$-$C_{12}$-Aralkyl radicals and $C_6$-$C_{10}$-aryl radicals can, by way of example, have the meanings given above. By way of example, $C_1$-$C_6$-alkoxycarbonyl radicals which may be mentioned are: methoxycarbonyl, ethoxycarbonyl, propoxycarbonyl and isopropoxycarbonyl, preferably methoxycarbonyl and ethoxycarbonyl.

Within the scope of a preferred embodiment of the method according to the invention, the cyclization of citronellal is carried out in the presence of a carboxylic anhydride of the formula (VI), where the radicals $R^{20}$ and $R^{20'}$ are identical and are a branched or unbranched $C_1$-$C_{12}$-alkyl radical or $C_7$-$C_{12}$-aralkyl radical or a $C_6$-$C_{10}$-aryl radical, and where $R^{20}$ and $R^{20'}$ can together also form a 5- to 8-membered ring which can have one or more ethylenic double bonds and one or more identical or different heteroatoms chosen from the group $OR^{10e}$, $SR^{10f}$, $NR^{11b}$, and $R^{10e}$, $R^{10f}$ and $R^{11b}$ can, independently of one another, have the meanings given above for $R^{11}$.

Particular preference is given to using those carboxylic anhydrides in which the radicals $R^{20}$ and $R^{20'}$ are identical and are a branched or unbranched $C_1$-$C_{12}$-alkyl radical or a $C_6$-$C_{10}$-aryl radical. By way of example, carboxylic anhydrides to be used particularly preferably according to the invention are: acetic anhydride, propionic anhydride, pivalic anhydride and benzoic anhydride.

Aldehydes of the formula (VII) which can likewise be used preferably according to the invention are, by way of example, acetaldehyde, propionaldehyde and chloral (trichloroacetaldehyde).

If, within the scope of a further preferred embodiment, the cyclization of citronellal is carried out in the presence of a ketone of the formula (VIII), it is advantageous to use those with an activated, i.e. electron-deficient, carbonyl function. By way of example, mention may be made of the following ketones which are particularly suitable for use within the scope of the method according to the invention: 1,1,1-trifluoroacetone, 1,1,1-trifluoroacetophenone, hexafluoroacetone, methyl pyruvate and ethyl pyruvate.

Vinyl ethers of the formula (IX) which can likewise be used with preference according to the invention are, for example: methyl vinyl ether, ethyl vinyl ether, isobutyl vinyl ether and 3,4-dihydro-2H-pyran.

The specified classes of compound can be used equally with good success within the scope of this preferred embodiment of the method according to the invention. With regard to practical aspects such as, for example, a higher reaction rate, the use of aldehydes and/or electron-deficient ketones has proven to be advantageous.

The amount of carboxylic anhydride, aldehyde, ketone and/or vinyl ether to be used according to the invention can be varied within wide limits and is governed by the type of substance used and the degree of purity or the presence of impurities which are as yet not more precisely identified. Usually, the specified compounds and mixtures thereof are used in an amount of from about 0.01 mol % to about 5 mol %, preferably from about 0.1 mol % to about 2 mol %, based on the amount of citronellal used.

The type and manner of the procedure, for example the configuration of reactors or the order in which individual reactants are added, are not subject to particular requirements provided a procedure with extensive exclusion of oxygen and water is ensured.

To carry out the method according to the invention within the scope of this preferred embodiment, the procedure advantageously involves firstly providing a solution of the bis(diarylphenoxy)aluminum compound to be used according to the invention in a suitable solvent as described above. Then, according to the invention, a mixture of the racemic or nonracemic citronellal to be cyclized with the chosen carboxylic anhydride, the aldehyde, the activated ketone and/or the vinyl ether is preferably added to this solution. Alternatively thereto, it is possible, for example, to also admix the solution of the bis(diarylphenoxy)aluminum compound to be used according to the invention firstly with the carboxylic anhydride, if appropriate chosen in each case, the aldehyde, the ketone and/or the vinyl ether, and to afterwards add the citronellal to be cyclized thereto.

It has proven to be advantageous to meter in the citronellal or the mixture of citronellal with the chosen compound to the catalyst solution or to the reaction mixture within a period of from about 30 min to about 6 h, preferably within about 2 h to about 4 h. The citronellal can here be added as such or in the form of a solution, advantageously in one of the abovementioned suitable solvents. Within the scope of an again preferred embodiment of the method according to the invention, a solution of the chosen ligand of the formulae (I) or (I.a) in toluene is firstly provided, and then the chosen aluminum compound of the formula (II) and/or (III), preferably trimethylaluminum or triethylaluminum in toluenic solution is added, expediently with stirring.

The addition of the citronellal to be cyclized or the mixture of citronellal with the chosen carboxylic anhydride, aldehyde, activated ketone and/or the vinyl ether takes place within the scope of this embodiment advantageously at temperatures in the range from about −40° C. to about 40° C., preferably in the range from about −20° C. to about 20° C. For this, the prepared solution or suspension of the bis(diarylphenoxy)aluminum compound according to the invention is advantageously cooled to a temperature within this range, e.g. to a temperature in the range from −10° C. to 10° C., and the other reactants are added in precooled form.

The addition of the mixture of citronellal and the chosen further compound can be undertaken so that either the total amount of citronellal is added in one go or it is added in portions or continuously to the prepared catalyst solution. Suitable solvents are in turn preferably the abovementioned solvents, in particular toluene. Preference is given to using the citronellal to be cyclized in the form of a mixture with the chosen carboxylic anhydride, aldehyde, activated ketone and/or vinyl ether without the further addition of solvents. When using a solvent, the total amount of solvent is advantageously chosen so that the volume-based ratio of citronellal to be reacted to the solvent is about 1:1 to about 1:20, preferably from about 1:1 to about 1:10.

It has been found that some of the catalyst complex is usually deactivated during the reaction. This is attributed, inter alia, to ligand exchange processes between the bis (diarylphenol) ligands of the formula used in each case of the bis(diarylphenoxy)aluminum compounds used and the isopulegol which forms as a result of cyclization. The deactivated form of the catalyst is, depending on the choice of solvent used, soluble in the reaction mixture, usually in contrast to the active polymeric catalyst.

In one preferred embodiment, the deactivated part of the catalyst can be separated off together with the other reaction mixture by simple physical separation methods (e.g. by filtering off or centrifuging the catalyst which is still active). The retained, still active part of the catalyst can, if desired, be supplemented with a fresh catalyst and be reused without appreciable loss in activity, preferably within the scope of a further cyclization reaction according to the invention of citronellal to isopulegol.

Alternatively, the amount of catalyst used can be chosen so that the total catalyst complex used is deactivated and thus soluble in the course of or at the end of the cyclization reaction according to the invention, something which is recognizable from a clear reaction mixture. Here, it is advantageously notable that in this case, on account of the abovedescribed ligand exchange processes, the bis(diarylphenol) ligand of the formula (I) used in each case is released without separate hydrolysis being carried out.

Surprisingly, it has been found that isopulegol can be distilled off from the aluminum-containing reaction products of the cyclization of citronellal without prior hydrolysis of the bis(diarylphenoxy)aluminum compounds used in each case as catalyst (if appropriate following distillative removal of a solvent used and/or additionally used auxiliaries) in high purities. As a rule, no recognizable undesired or troublesome by-products form here in the distillation bottom. In a specific embodiment, a suitable, inert, high-boiling solvent is added before or during the distillative separation in step a). A solution of the ligand of the formula (I) in the heated high-boiling component used in each case is then obtained in the distillation bottom.

As already mentioned, the method according to the invention is equally suitable for cyclizing racemic and nonracemic, i.e. optically active, citronellal to give racemic and nonracemic isopulegol.

In a preferred embodiment, the method according to the invention thus serves for producing optically active isopulegol of the formula (IV.a)

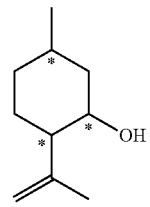

(IV.a)

by cyclization of active citronellal of the formula (V.a)

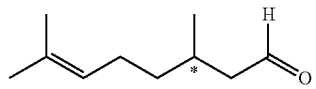

(V.a)

where (*) in each case refers to an asymmetric carbon atom.

The method according to the invention serves in particular for producing L-(−)-isopulegol by cyclization of D-(+)-citronellal.

The racemic or nonracemic isopulegol produced in this way is a valuable intermediate for producing racemic or nonracemic menthol, one of the most significant fragrances or aromas worldwide. Menthol can be obtained from isopulegol by methods of hydrogenation known per se to the person skilled in the art, specifically catalytic hydrogenation over suitable transition metal catalysts, as described, for example, in Pickard et al., J. Chem. Soc. 1920, 1253; Ohloff et al., Chem. Ber. 1962, 95, 1400; Pavia et al., Bull. Soc. Chim. Fr. 1981, 24, Otsuka et al., Synthesis 1991, 665 or in EP 1 053 974 A. Here, if the chosen reaction conditions are suitable, the relative or absolute configuration of the isopulegol used is largely retained, and in many cases is completely retained.

The present invention therefore further provides a method of producing menthol comprising the steps:

A) production of isopulegol of the formula (IV) by a method according to the invention B) hydrogenation of the ethylenic double bond of the isopulegol obtained in this way.

In a preferred embodiment, this method serves for producing optically active menthol, specifically for producing L-(−)-menthol from optically active L-(−)-isopulegol.

With regard to the preferred embodiments of the method according to the invention for producing isopulegol, reference is made to the abovementioned preferences in their entirety.

Embodiments of the invention are illustrated below with reference to the drawings.

Figure 2:
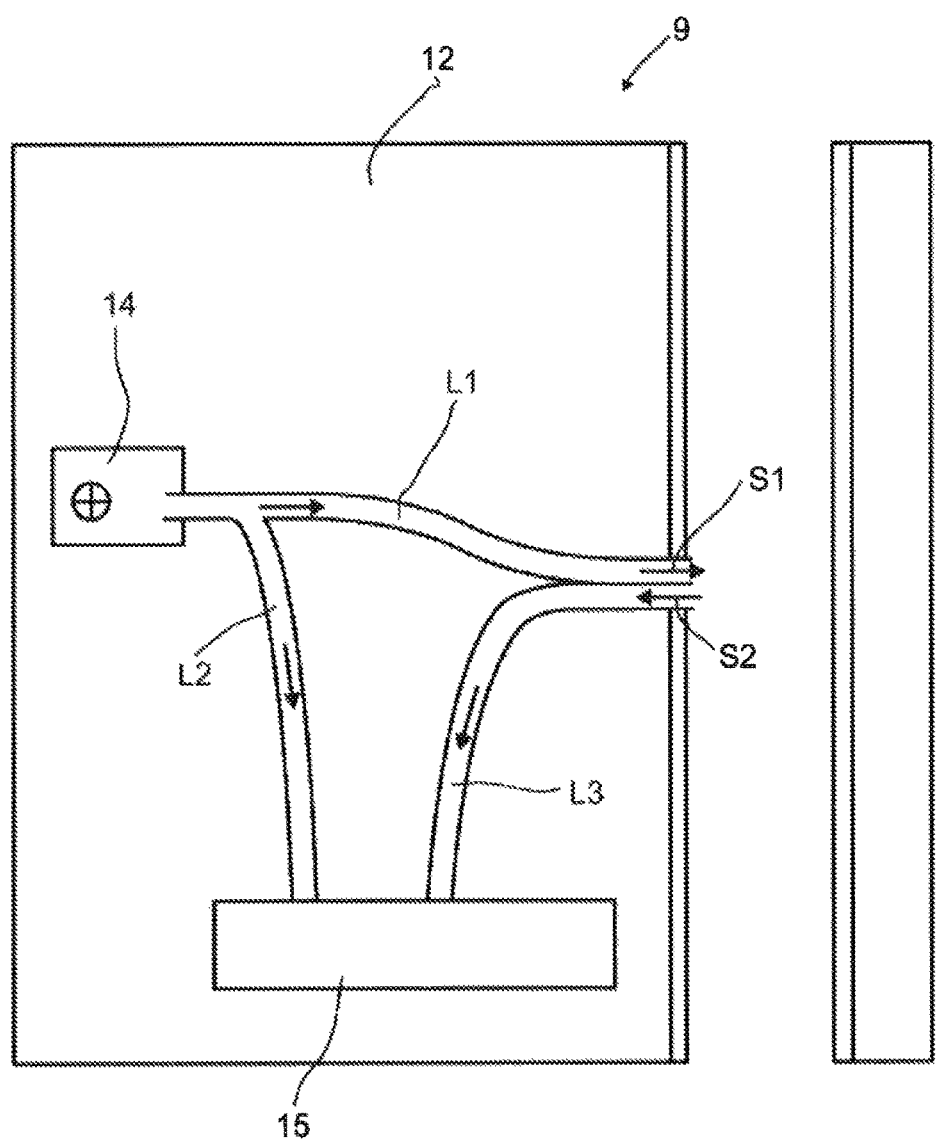
Figure 3:
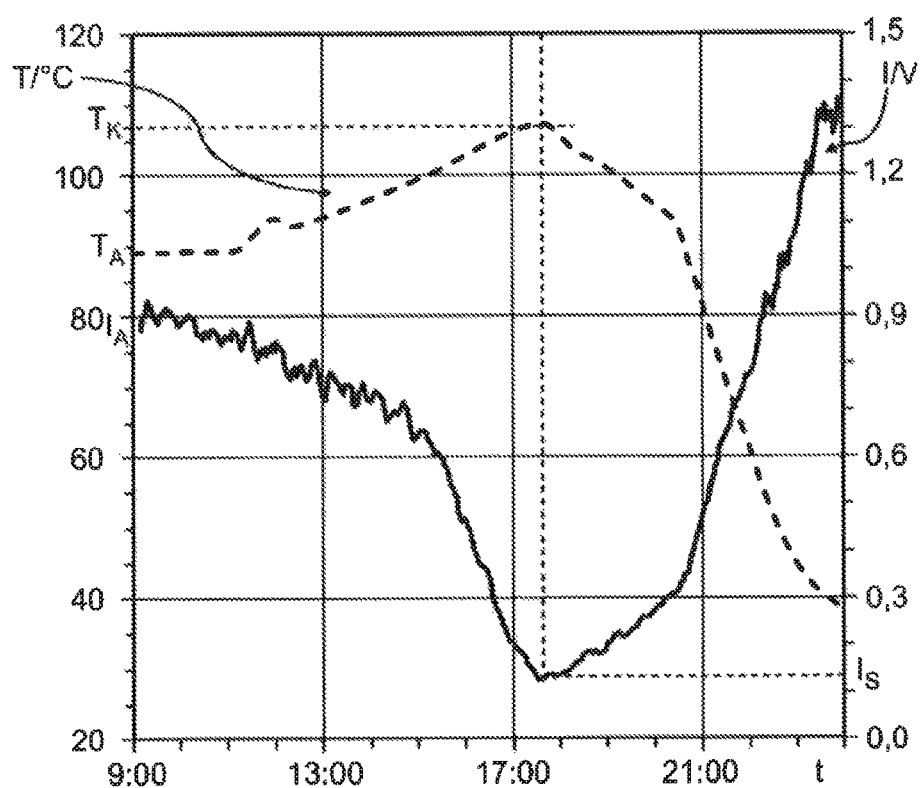
Figure 4:
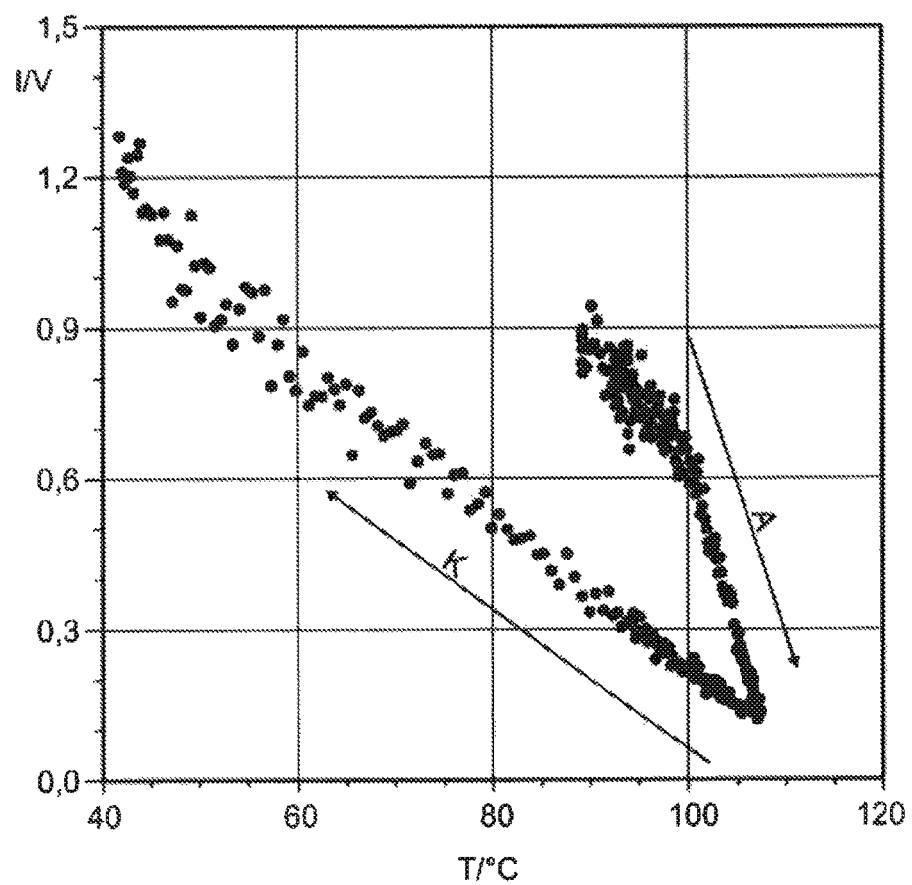
Figure 5:
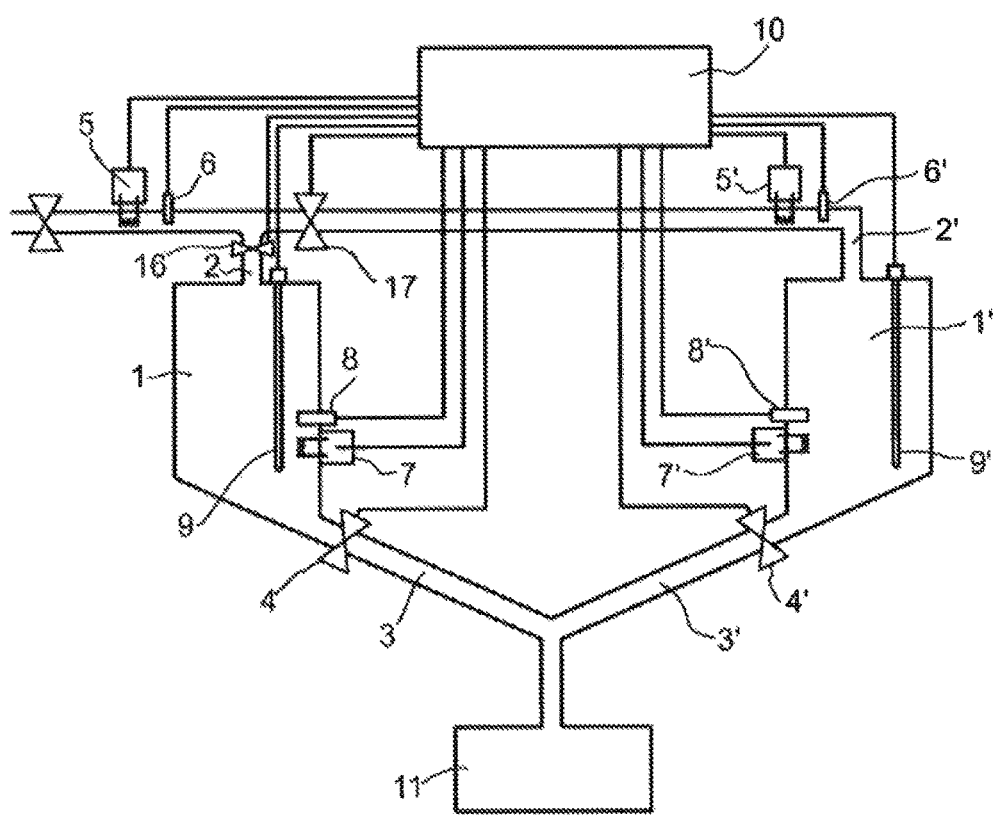

FIG. 1 shows the design of a first embodiment of the device according to the invention for separating off a substance from a solution, FIG. 2 shows the design of the scattered-light probe which is used in the embodiment shown in FIG. 1, FIG. 3 shows a diagram in which an example of the temperature course and of the detected intensity is plotted for an embodiment of the method according to the invention, FIG. 4 shows a diagram which illustrates the relationship between the detected intensity and the temperature for an embodiment of the method according to the invention, and FIG. 5 shows a further embodiment of the device according to the invention.

With reference to FIG. 1, the design of the first embodiment of the device according to the invention for separating off a substance from a solution is explained:

The device comprises a crystallization vessel 1 which has a feed line 2 and a discharge line 3. The solution is introduced into the crystallization vessel 1 via the feed line 2. So that the introduced solution remains firstly in the crystallization vessel 1, an electronically controllable valve 4 is provided in the discharge line 3 which is initially closed. After the crystallization method has been carried out in the crystallization vessel 1, the suspension with the crystals is discharged from the crystallization vessel 1 via the discharge line 3.

A heating device 5 is provided in the feed line 2 or alternatively in a storage vessel. By means of this heating device 5 it is possible to regulate the temperature of the solution which is introduced into the crystallization vessel 1 via the feed line 2. For the temperature regulation, a temperature sensor 6 is furthermore provided in the feed line 2. Furthermore, a heating device 7 and a temperature sensor 8 are also provided in the crystallization vessel 1, by means of which the temperature of the solution that is located in the crystallization vessel 1 is measured and regulated.

Finally, a scattered-light probe 9, which is explained in detail later, is located within the crystallization vessel 1. The valve 4, the heating devices 5 and 7, the temperature sensors 6 and 8, as well as the scattered-light probe 9 are data-coupled with a regulating unit 10. In this way, the measurement values of the temperature sensors 6 and 8 and the measurement values of the scattered-light probe 9 are conveyed to the regulating unit 10. Furthermore, the regulating unit 10 controls the light emission of the scattered-light probe 9, as is explained later, and the heating or cooling output of the heating devices 5 and 7. Furthermore, the valve 4 can be opened and closed by means of the regulating unit 10.

The discharge line 3 through which the suspension is removed from the crystallization vessel 1 is connected to a separation unit 11. The separation unit 11 can be configured as a filter device known per se.

With reference to FIG. 2, the scattered-light probe 9 is described in detail below:

The scattered-light probe 9 comprises a tube 12 in which the waveguides L1 and L3 are located. At the end of the tube 12, which dips into the crystallization vessel 1, the waveguide L1 has a decoupling area and the waveguide L3 has a coupling area.

In the scattered-light probe 9, a radiation source 14 or an emitter for electromagnetic radiation is provided. The electromagnetic radiation emitted by the radiation source 14 is coupled via a coupling area in the waveguide L1, via which the electromagnetic radiation is conveyed to the decoupling area of the waveguide L1. The electromagnetic radiation generated by the radiation source 14 is thus radiated as radiation S1 into the solution located in the crystallization vessel 1.

The beam generated by the radiation S1 has, upon entering into the solution or suspension, a cross section greater than 0.39 mm. Furthermore, the beam with an angle of about +/−12° is divergent, i.e. the aperture angle of the beam is 24°.

The waveguides L1 and L3 are passed through the opening 13 of the scattered-light probe 9 in a parallel and liquid-tight manner. They are in particular configured such that the direction of the radiation S1 radiated into the solution or suspension is parallel to the detection direction for the radiation S2 which has been scattered at the crystals and which is coupled into the waveguide L3. The tube 12 of the scattered-light probe 9 is dipped into the crystallization vessel 1 such that, in the event of a clear solution for which no crystals are present in the solution, no radiation arrives in the waveguide L3 which has a wavelength in which the radiation source 14 emits radiation if radiation is emitted into the clear solution via the waveguide L1.

The beam of the incident radiation S2 which enters the waveguide L3 is also divergent with the same aperture angle, meaning that the emitting and receiving range of the scattered-light probe 9 is spatially overlapping. This gives rise to two adjoining cones which intersect spatially. This gives rise to a very large measurement volume, which is important particularly in the case of very low particle concentrations.

The scattered-light probe 9 has no disk as termination between the waveguides L1 and L3 on the one hand and the solution or suspension on the other hand. The optical offset of the scattered-light probe 9 therefore approaches zero.

In the embodiment described here, the radiation source 14 generates infrared radiation in a wavelength range from 800 nm to 900 nm. The electromagnetic radiation radiated into the solution is scattered onto the surfaces of crystals which are located in the solution. Some of the electromagnetic radiation S2 back-scattered at the crystals is conveyed via the coupling area of the waveguide L3 from this to a detector 15. The detector 15 is configured such that it can measure the intensity of the electromagnetic radiation in the wavelength range in which the radiation source 14 emits electromagnetic radiation.

The detector 15 has a receiving electronic unit which permits a very wide intensification range from 2 mW/V to 20 picoW/V. This means that the receiving electronic unit produces a voltage of 1 V for an incident light intensity of 20 picoW, i.e. at a light intensity of about 150 μLux/cm². Consequently, the detector 15 is extremely sensitive.

A diversion is also provided in the waveguide L1. Some of the radiation generated by the radiation source 14 and coupled in the waveguide L1 is diverted to a waveguide L2 and passed to the detector 15. The radiation diverted via the waveguide L2 and passed to the detector 15 serves as reference radiation.

In the detector 15, a voltage level is generated which is directly related to the light intensity back-scattered by the crystals in the solution. The reference voltage level generated by the detector 15, which is brought about by the reference radiation, takes into consideration here the intensity of the radiation S1 radiated into the solution. The voltage level of the detector 15 is corrected in an evaluation unit, taking into consideration the reference voltage level of the detector 15, and transferred to the regulating unit 10.

The scattered-light probe 9 used can for example be a variation of the photometric measuring device, as described in EP 0 472 899 A1. The scattered-light probe described in this specification can be used both for a transmission measurement and for a back scatter measurement. In the present case, the back scatter measurements would be taken into consideration.

In a further variant, the scattered-light probe 9 comprises a rod probe which is dipped into the crystallization vessel 1. The detector 15 is then connected to the rod probe via waveguides and arranged outside of the crystallization vessel 1.

The measurement can furthermore also be carried out with a detector 15 without referencing the radiation source 14. However, for the long-term stability of the measurement, the referencing with a second detector is advantageous. The correction of the scattered signal that is detected by the detector 15 then takes place by reference to the reference signal that is detected by a further detector in an evaluation unit which then generates a corrected scattered signal and conveys it to the regulating unit 10.

Either one or more waveguides can serve as emitters and receivers in the rod probe. The fiber geometry does not necessarily have to be realized with parallel emitting and receiving fibers, although this is preferred. Furthermore, a solution with disk before the fiber ends with deviating geometry could also be used, although then, on account of the internal reflections, this leads to a considerably higher signal offset and consequently to a significantly lower sensitivity of the measuring system especially in the case of very low particle concentrations.

The scattered-light probe 9 does not detect the complete scattered radiation. On account of multiple scattering, transmission and absorption and on account of the spatially limited receiving cone (aperture), the scattered-light probe 9 detects only a fraction of the scattered radiation proportional to the particle surface.

Further details of the device according to the invention as well as an embodiment of the method according to the invention are explained in the detail below:

In the described embodiment, the aim is to separate off the ligand Ia$_2$-3 described at the start, which is dissolved in phenylcyclohexane. The solution was obtained as bottom product from the cyclization of citronellal in the presence of a (bis(diarylphenoxy))aluminum catalyst. This solution gives rise to the problem that the complex chemical method carried out beforehand leads to the precise composition of the solution and the establishing concentrations of dissolving and nondissolving secondary components not being known exactly and therefore the saturation temperature at which the ligand crystallizes can fluctuate greatly.

According to the invention, reference measurements are therefore carried out beforehand. The reference measurements can advantageously also be carried out in the laboratory. Here, the solution is introduced into the crystallization vessel 1 at a temperature which is a few 10 K below the expected saturation temperature. For example, the solution is introduced at a temperature of 80° C. This temperature is adjusted by means of the regulating unit 10, the heating devices 5 and 7 and the temperature sensors 6 and 8. At this temperature, a very large amount of crystals of the ligand is in the solution. However, the crystal size and morphology of the crystals is unsuitable for subsequent filtration in the separation unit 11. The temperature of the solution which is introduced into the crystallization vessel 1 is now raised by means of the heating device 5. At the same time, by means of the scattered-light probe 9 electromagnetic radiation is radiated into the solution. The temperature of the solution is then continuously determined by the regulating unit 10 by means of the temperature sensor 8. In addition, the intensity of the back-scattered electromagnetic radiation is ascertained by reference to the voltage level conveyed by the evaluation unit. During the increase in temperature, the signal for the intensity of the back-scattered electromagnetic radiation decreases since the crystals dissolve and the crystal surface available for the back-scattering is thus reduced.

As a result of the reference measurements, the intensity of the detected electromagnetic radiation is determined at which an amount of seed crystals of the ligand or a crystal surface of this seed crystal is present which is ideal for a subsequently carried out crystallization method in which the solution is cooled again and crystals are supposed to form which have a crystal size and morphology ideal for the subsequent separation. In the case of the reference measurements, the temperature of the solution is therefore increased until the intensity of the back-scattered electromagnetic radiation has dropped to a certain value. Consequently, a cooling crystallization method is started in a manner known per se in which, with a certain cooling curve, the solution is cooled again such that crystals of the ligand are formed. The crystals are then filtered out in the separation unit 11, and the size and morphology of these crystals is investigated.

The reference measurements are now carried out for a large number of intensities, for which the subsequent crystallization method is always carried out in the same way. The reference measurement is then determined at which the crystal size and morphology ideal for the separation have been generated. The intensity of the back-scattered electromagnetic radiation at the start of the crystallization method of this reference measurement, i.e. the minimum intensity of the back-scattered electromagnetic radiation at this reference measurement, is defined as desired intensity $I_S$. At this desired intensity Is, the size of the crystal area which is formed by the seed crystals of the ligand is ideal for the subsequently carried out crystallization method.

Furthermore, a starting temperature value $T_A$ is stipulated beforehand at which the solution is introduced into the crystallization vessel 1 at the start of the method. This starting temperature value $T_A$ is clearly below the temperature value $T_K$ which corresponds to the desired intensity Is, i.e. the starting temperature for the crystallization method. In the present example, the starting temperature value $T_A$ is about 90° C. This starting temperature value $T_A$ can moreover also be determined from the desired intensity $I_S$ by selecting the starting intensity $I_A$ assigned to the starting temperature value $T_A$ for the back-scattered electromagnetic radiation as the x-fold intensity of the desired intensity $I_S$. The value x here can be in a range from 1.2 to 10. In the present case, the value x is 6.5.

The method for separating off the ligand from the solution introduced via the feed line 2 is then carried out as follows following the determination of the desired intensity and the starting temperature value:

The solution is introduced via the feed line 2 with the starting temperature value $T_A$. As soon as enough solution has been introduced into the crystallization vessel 1 that the scattered-light probe 9 is located within the solution, the intensity I of the electromagnetic radiation back-scattered at the crystals is determined by the regulating unit 10.

In FIG. 3, the course over time of the signal I of the scattered-light probe 9, which correlates with the intensity I of the back-scattered electromagnetic radiation, as well as the associated course over time of the temperature T of the solution is shown. The starting temperature value $T_A$ in this case is 89.13° C. The associated signal $I_A$ of the scattered-light probe 9 is 0.85 V. Conceptually, no distinction is made hereinbelow between the signal I of the scattered-light probe 9 and the intensity I of the back-scattered electromagnetic radiation since these are directly related.

The temperature of the solution introduced into the crystallization vessel 1 via the feed line 2 is now increased by means of the regulating unit 10. As is evident from FIG. 3, the temperature of the solution within the crystallization vessel 1 thus also increases. At the same time, the signal I of the scattered-light probe 9 drops since the crystals of the ligand dissolve. The temperature of the introduced solution is raised until the signal I of the scattered-light probe 9 is within a tolerance range around the desired intensity $I_S$. In other words, this means that the amount of difference between the detected intensity I and the desired intensity $I_S$ is less than a limiting value. This limiting value can for example be 10% of the desired intensity $I_S$.

In the ideal case, in the event of the complete filling of the crystallization vessel 1, the amount of difference between the detected intensity I and the desired intensity $I_S$ is less than this limiting value. If this is not the case, the temperature of the solution located within the crystallization vessel 1 is also finely adjusted via the heating device 7 and the regulating unit 10 until the amount of this difference is below this limiting value.

In this state of the solution located in the crystallization vessel 1, the ideal amount of seed crystals of the ligand determined in the reference measurements is present with the ideal crystal surface. The actual cooling crystallization method is now started. Regulated by the regulating unit 10, the solution is cooled firstly at a low cooling rate of about 3 K/h. After a certain time, i.e. when a certain amount of crystals of a certain size is present, the cooling rate can for example be increased to about 20 K/h. In this way, crystals of the ligand which have a crystal size and morphology ideal for the subsequent separation are formed within the shortest possible time. The suspension with the crystals is then supplied, by opening the valve 4 and via the discharge line 3, to the separation unit 11, in which the suspension is filtered and the ligand of the formula Ia$_2$-3 can be obtained as a white solid.

FIG. 4 shows the relationship between the detected intensity I of the electromagnetic radiation scattered at the crystals and the temperature T, specifically for the measurement values shown in FIG. 3. The measurement values for arrow A show the dissolution of the crystals at the start of the method, i.e: before the actual crystallization method, and the measurement values along arrow K show the crystallization during the crystallization method which was started at the intensity $I_S$ and temperature $T_K$.

A clear difference arises in the case of the curve for the dissolution, i.e. while raising the temperature to the desired intensity Is, and the curve for the subsequent crystallization, i.e. while lowering the temperature starting with the temperature value $T_K$. At the same temperature, the intensity measured by the scattered-light probe 9 during the dissolution is substantially higher than during the crystallization. During the dissolution, the crystals of the ligand thus have a greater specific surface area. This means that they are very finely divided. These are thus small crystals. This is undesired for the subsequent separation of the crystals. During the subsequent crystallization, the intensity of the signal measured by the scattered-light probe 9, by contrast, is smaller by a factor of 2 to 3. At a certain temperature, however, the same mass of crystals is in solution. The lower intensity of the back-scattered radiation therefore indicates that the specific surface area of the crystals is smaller. It is evident from this that the crystals are larger, as is desired for the subsequent separation of the crystals.

A second embodiment of the device according to the invention and of the method according to the invention is explained below with reference to FIG. 5:

The device of the second embodiment comprises the device of the first embodiment shown in FIG. 1. The same parts are therefore labeled with the same reference numerals. Accordingly, reference is made to the above description of these parts. The device of the second embodiment shown in FIG. 5, however, has a further crystallization vessel 1'. Like the first crystallization vessel 1, the second crystallization vessel 1' comprises a feed line 2', a discharge line 3' with a valve 4'. Provided in the feed line 2' are a heating device 5' and a temperature sensor 6' for regulating the temperature of the solution which is introduced into the second crystallization vessel 1'. Provided for the second crystallization vessel 1' are a heating device 7' and a temperature sensor 8', and a further scattered-light probe 9'. The valve 4', the heating devices 5' and 7', the temperature sensors 6' and 8', and the scattered-light probe 9' are data-coupled with the regulating unit 10.

Furthermore, an electronically controlled valve 16 is arranged in the feed line 2 for the first crystallization vessel 1; similarly an electronically controllable valve 17 is arranged in the feed line 2' for the second crystallization vessel 1'. Valves 16 and 17 are also data-coupled with the regulating unit 10.

According to a second embodiment of the method according to the invention, the device shown in FIG. 5 is operated as follows:

As explained with reference to FIGS. 1 to 3, the solution is introduced into the first crystallization vessel 1 via the feed line 2. In this case, the valve 16 is opened and the valve 17 is closed, meaning that no solution passes into the second crystallization vessel 1'. Upon introducing the solution, the temperature is regulated as explained above such that the temperature of the solution in the first crystallization vessel 1, if this is filled completely, corresponds to the temperature value $T_K$, which is assigned to the desired intensity $I_S$ at which the desired amount of seed crystals is present.

The valve 16 is then closed and, in the first crystallization vessel 1, the cooling crystallization starts, in which the temperature of the solution in the first crystallization vessel 1 is reduced. At the same time, by means of the heating device 5 and the temperature sensor 6, the temperature of the solution to be introduced is again brought to the starting temperature value $T_A$. The valve 17 is then opened so that the solution is conveyed to the second crystallization vessel 1'. By means of the heating device 5' and the temperature sensor 6', the temperature of the solution conveyed to the second crystallization vessel 1' is then regulated such that the intensity of the back-scattered radiation measured by the scattered-light probe 9' is close to the desired intensity Is, as has already been described above for the first crystallization vessel 1. As soon as the amount of difference between the detected intensity and the desired intensity $I_S$ is less than the limiting value, the valve 17 is closed and, in the second crystallization vessel 1', the cooling crystallization method is carried out as described above, in which the temperature of the solution is reduced so that crystals of the ligand are formed. While the crystallization process in the second crystallization vessel 1' is carried out, the crystallization process in the first crystallization vessel 1 is concluded and the valve 4 is opened so that the suspension is fed to the separation unit 11 via the discharge line 3. The crystals of the ligand are isolated in the separation unit 11. During this, the valve 4 can be closed again, and the solution is again passed to the first crystallization vessel 1.

If the crystallization process is concluded in the second crystallization vessel 1', the crystals that have been supplied to the separation unit 11 via the discharge line 3 have already been isolated from the suspension of the first crystallization vessel 1. The valve 4' can now be opened such that the suspension with the crystals of the ligand can be supplied, from the second crystallization vessel 1' and via the discharge line 3', to the separation unit 11. There, the crystals of the ligand are then filtered out.

In this way, the device shown in FIG. 5 can be used to carry out the method described above with reference to FIG. 1 alternately in the two crystallization vessels 1 and 1'.

An embodiment of the method for working up an aluminum-containing reaction product from the preparation of isopulegol by cyclizing citronellal is described below:

The aluminum-containing reaction product is worked up, as described in WO 2008/025852 A1. In the last process step, the ligand of the formula Ia$_2$-3 is obtained, as has been described above with reference to FIGS. 1 to 5.

A further embodiment of the invention relates to a method for producing isopulegol. In this embodiment, isopulegol is prepared as described in WO 2008/025852 A1. In contrast to the method described in this specification, however, the ligand is separated off from the organic phase according to an embodiment as has been described above with reference to FIGS. 1 to 5.

A yet further embodiment relates to a method for producing menthol. In this case, isopulegol is prepared as described above. Menthol is then prepared by hydrogenation of the ethylenic double bond of the isopulegol obtained in this way.

LIST OF REFERENCE NUMERALS 1, 1' Crystallization vessel
2, 2' Feed line
3, 3' Discharge line
4, 4' Valve
5, 5' Heating device
6, 6' Temperature sensor
7, 7' Heating device
8, 8' Temperature sensor
9, 9' Scattered-light probe
10 Regulating unit
11 Separation unit
12 Tube
14 Radiation source for electromagnetic radiation
15 Detector
16 Valve
17 Valve

The invention claimed is:

1. A method for separating off a substance by crystallization from a solution of the substance, in which
a suspension of seed crystals is produced and, when a desired amount of seed crystals is present, a crystallization method is started, in which crystals of the substance are obtained which are then separated off, where, for producing the desired amount of seed crystals: electromagnetic radiation is radiated into the solution, where the electromagnetic radiation radiated into the solution has the form of a beam, an aperture angle of which is greater than 5 degrees,
for establishing a desired amount of seed crystals an intensity of the electromagnetic radiation which has been scattered by crystals located in the solution is detected and then the crystallization method is started, the detected intensity is compared with a desired intensity ($I_S$),
the temperature of the solution is regulated depending on any difference between the detected intensity and the desired intensity ($I_S$) in such a way that an amount of this difference is reduced,
if the amount of the difference between the detected intensity and the desired intensity ($I_S$) is less than a limiting value, the desired amount of seed crystals for the crystallization method is present, wherein the desired intensity ($I_S$) is determined by reference measurements by which, for the solution, the relationship between the crystal size and/or the crystal morphology at an end of the crystallization method and the detected intensity at the start of the crystallization method is determined and from this the desired intensity ($I_S$) is selected as the intensity for the desired crystal size and/or crystal morphology.

2. The method according to claim 1, wherein the solution or some of the solution is brought in a crystallization vessel to a temperature which is lower than a defined starting temperature value ($T_A$), which is below an anticipated saturation temperature of the solution, and the solution is then heated until the amount of difference between the detected intensity and the desired intensity ($I_S$) is less than the limiting value.

3. The method according to claim 1, wherein the starting temperature value ($T_A$) is determined from the desired intensity ($I_S$) by selecting the starting intensity ($I_A$) assigned to a starting temperature value ($T_A$) as the x-fold intensity of the desired intensity ($I_S$), where the value x is in a range from 1.2 to 10, and the temperature of the solution is regulated in such a way until the intensity is greater than the starting intensity ($I_A$).

4. The method according to claim 1, wherein the electromagnetic radiation comprises one or more wavelength ranges which are wider than 20 nm radiated into the solution.

5. The method according to claim 1, wherein the electromagnetic radiation radiated into the solution has the form of a beam, the minimum cross section of which is greater than 0.1 mm.

6. The method according to claim 1, wherein the electromagnetic radiation radiated into the solution is infrared radiation and the intensity of infrared radiation is detected.

7. The method according to claim 1, wherein the electromagnetic radiation is radiated into the solution by means of a scattered-light probe (9) and the intensity of a back-scattered electromagnetic radiation is detected by means of the scattered-light probe (9).

8. The method according to claim 1, wherein an incident direction of the radiated electromagnetic radiation is essentially parallel to a detection direction, from which the intensity of the back-scattered electromagnetic radiation is detected.

9. The method according to claim 1, wherein
the solution is introduced into a crystallization vessel (1) at a temperature which is below a starting temperature value ($T_A$),
if the scattered-light probe (9) is located within the introduced solution, the electromagnetic radiation is radiated into the solution by means of the scattered-light probe (9) and the intensity of the electromagnetic radiation which has been scattered by the crystals located in the solution is detected, and
the temperature of the solution upon further introduction of the solution into the crystallization vessel (1) is regulated such that the amount of difference between the detected intensity and the desired intensity ($I_S$) is less than the limiting value.

10. The method according to claim 1, wherein the material comprises at least one ligand of the formula (I)

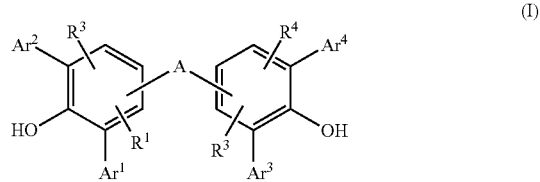

49 where
Ar¹, Ar², Ar³, Ar⁴, independently of one another, are chosen from $C_6$-$C_{15}$-aryl radicals or $C_2$-$C_{15}$-heteroaryl radicals, which, if appropriate, can in each case carry 1 to 7 identical or different substituents chosen from $C_1$-$C_6$-alkyl, $C_1$-$C_6$-perfluoroalkyl, $C_1$-$C_6$-alkoxy, $C_7$-$C_{12}$-aralkyl, halogen, $SiR^{5a}R^{6a}R^{7a}$, optionally substituted $C_6$-$C_{10}$-aryl, $NR^{8a}R^{9a}$, $SR^{10a}$, $NO_2$, R¹, R², R³, R⁴, independently of one another, are chosen from hydrogen, $C_1$-$C_6$-alkyl, $C_1$-$C_6$-perfluoroalkyl, $C_1$-$C_6$-alkoxy, $C_7$-$C_{12}$-aralkyl, halogen, $SiR^{5b}R^{6b}R^{7b}$, optionally substituted $C_6$-$C_{10}$-aryl, $NR^{8b}R^{9b}$, $SR^{10b}$, $NO_2$ and where R¹ or R² and/or R³ or R⁴, together with A, form an aromatic or nonaromatic cycle, and A is a straight-chain or branched and/or cyclic hydrocarbon radical having 1 to 25 carbon atoms which may be saturated or mono- or polyunsaturated and/or partially aromatic and, if appropriate, have one or more identical or different heteroatoms chosen from O, S, $NR^{11}$, and/or one or more identical or different functional groups chosen from the functional groups C(O), S(O), S(O)₂ and, if appropriate, carry one or more identical or different substituents chosen from the substituents $C_1$-$C_6$-alkyl, $C_1$-$C_6$-perfluoroalkyl, $C_1$-$C_6$-alkoxy, $C_1$-$C_{10}$-acyloxy, $C_7$-$C_{12}$-aralkyl, halogen, —$SiR^{5c}R^{6c}R^{7c}$, optionally substituted $C_6$-$C_{10}$-aryl, substituted or unsubstituted $C_2$-$C_{10}$-hetaryl, $NR^{8c}R^{9c}$, $SR^{10c}$, $NO_2$, $C_1$-$C_{12}$-acyl, $C_1$-$C_{10}$-carboxyl, or is a C6-C15-aryl radical or a C2-C15-heteroaryl radical which, if appropriate, in each case carry 1 to 5 substituents chosen from $C_1$-$C_6$-alkyl, $C_1$-$C_6$-perfluoroalkyl, $C_1$-$C_6$-alkoxy, $C_7$-$C_{12}$-aralkyl, halogen, $SiR^{5d}R^{6d}R^{7d}$, substituted or unsubstituted $C_6$-$C_{10}$-aryl, $NR^{8d}R^{9d}$, $SR^{10d}$, $NO_2$, or is a functional group or a heteroatom chosen from the group —O—, —S—, —N($R^{11}$)—, —S(O)—, —C(O)—, —S(O)₂—, —P($R^{11}$)—, —($R^{11}$)P(O)— and —Si($R^{12}R^{13}$), where the radicals $R^{5a}$, $R^{6a}$, $R^{7a}$, $R^{8a}$, $R^{9a}$, $R^{10a}$ to $R^{5d}$, $R^{6d}$, $R^{7d}$, $R^{8d}$, $R^{9d}$, $R^{10d}$, $R^{11}$, $R^{12}$ and $R^{13}$ are in each case independently of one another chosen from $C_1$-$C_6$-alkyl, $C_7$-$C_{12}$-aralkyl and/or substituted or unsubstituted $C_6$-$C_{10}$-aryl and where the radicals $R^{8a}$ and $R^{9a}$, $R^{8b}$ and $R^{9b}$, $R^{8c}$ and $R^{9c}$, $R^{8d}$ and $R^{9d}$, independently of one another, in each case together also form a cyclic hydrocarbon radical having 2 to 8 carbon atoms which have one or more identical or different heteroatoms chosen from the group O, S, $NR^{11a}$, and $R^{11a}$ have the meanings given for $R^{11}$, in free and/or complex-bound form.

11. The method according to claim 10, wherein the solution or some of the solution is brought in a crystallization vessel (1) to a temperature which is less than 95° C.

12. A method for obtaining a substance from a solution by means of crystallization, in which the solution is introduced into a first crystallization vessel (1) and the substance is separated off by means of crystallization in the first crystallization vessel (1) by the method according to claim 1 and in which, while carrying out the crystallization method in the first crystallization vessel (1), the solution is introduced into a second crystallization vessel (1') and the substance is separated off by means of crystallization in the second crystallization vessel (1') by the process according to claim 1.

50

13. A method for working up an aluminum-containing reaction product from the production of isopulegol by cyclizing citronellal, comprising
i) isopulegol,
ii) at least one ligand of the formula (I),

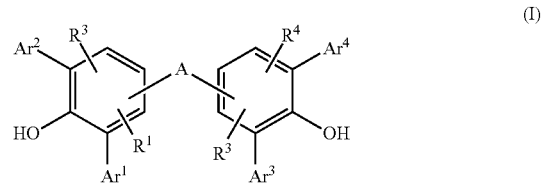

where
Ar¹, Ar², Ar³, Ar⁴, independently of one another, are chosen from $C_6$-$C_{15}$-aryl radicals or $C_2$-$C_{15}$-heteroaryl radicals, which, if appropriate, in each case carry 1 to 7 identical or different substituents chosen from $C_1$-$C_6$-alkyl, $C_1$-$C_6$-perfluoroalkyl, $C_1$-$C_6$-alkoxy, $C_7$-$C_{12}$-aralkyl, halogen, $SiR^{5a}R^{6a}R^{7a}$, optionally substituted $C_6$-$C_{10}$-aryl, $NR^{8a}R^{9a}$, $SR^{10a}$, $NO_2$, R¹, R², R³, R⁴, independently of one another, are chosen from hydrogen, $C_1$-$C_6$-alkyl, $C_1$-$C_6$-perfluoroalkyl, $C_1$-$C_6$-alkoxy, $C_7$-$C_{12}$-aralkyl, halogen, $SiR^{5b}R^{6b}R^{7b}$, optionally substituted $C_6$-$C_{10}$-aryl, $NR^{8b}R^{9b}$, $SR^{10b}$, $NO_2$ and where R¹ or R² and/or R³ or R⁴, together with A, form an aromatic or nonaromatic cycle, and A is a straight-chain or branched and/or cyclic hydrocarbon radical having 1 to 25 carbon atoms which may be saturated or mono- or polyunsaturated and/or partially aromatic and, if appropriate, have one or more identical or different heteroatoms chosen from O, S, $NR^{11}$, and/or one or more identical or different functional groups chosen from the functional groups C(O), S(O), S(O)₂ and, if appropriate, carry one or more identical or different substituents chosen from the substituents $C_1$-$C_6$-alkyl, $C_1$-$C_6$-perfluoroalkyl, $C_1$-$C_6$-alkoxy, $C_1$-$C_{10}$-acyloxy, $C_7$-$C_{12}$-aralkyl, halogen, —$SiR^{5c}R^{6c}R^{7c}$, optionally substituted $C_6$-$C_{10}$-aryl, substituted or unsubstituted $C_2$-$C_{10}$-hetaryl, $NR^{8c}R^{9c}$, $SR^{10c}$, $NO_2$, $C_1$-$C_{12}$-acyl, $C_1$-$C_{10}$-carboxyl, or is a $C_6$-$C_{15}$-aryl radical or a $C_2$-$C_{15}$-heteroaryl radical which, if appropriate, in each case carry 1 to 5 substituents chosen from $C_1$-$C_6$-alkyl, $C_1$-$C_6$-perfluoroalkyl, $C_1$-$C_6$-alkoxy, $C_7$-$C_{12}$-aralkyl, halogen, $SiR^{5d}R^{6d}R^{7d}$, substituted or unsubstituted $C_6$-$C_{10}$-aryl, $NR^{8d}R^{9d}$, $SR^{10d}$, $NO_2$, or is a functional group or a heteroatom chosen from the group —O—, —S—, —N($R^{11}$)—, —S(O)—, —C(O)—, —S(O)₂—, —P($R^{11}$)—, —($R^{11}$)P(O)— and —Si($R^{12}R^{13}$), where the radicals $R^{5a}$, $R^{6a}$, $R^{7a}$, $R^{8a}$, $R^{9a}$, $R^{10a}$ to $R^{5d}$, $R^{6d}$, $R^{7d}$, $R^{8d}$, $R^{9d}$, $R^{10d}$, $R^{11}$, $R^{12}$ and $R^{13}$ are in each case independently of one another chosen from $C_1$-$C_6$-alkyl, $C_7$-$C_{12}$-aralkyl and/or substituted or unsubstituted $C_6$-$C_{10}$-aryl and where the radicals $R^{8a}$ and $R^{9a}$, $R^{8b}$ and $R^{9b}$, $R^{8c}$ and $R^{9c}$, $R^{8d}$ and $R^{9d}$, independently of one another, can in each case together also form a cyclic hydrocarbon radical having 2 to 8 carbon atoms which have one or more identical or different heteroatoms chosen from the group O, S, $NR^{11a}$, and $R^{11a}$ have the meanings given for $R^{11}$, in free and/or complex-bound form, in which a) the reaction product is subjected to distillative separation to obtain an isopulegol-enriched top product and an isopulegol-depleted bottom product,
b) the isopulegol-depleted bottom product is brought into close contact with an aqueous base to give an aluminum-containing aqueous phase and an organic phase comprising the majority of the ligands of the formula (I),
c) the ligand of the formula (I) is separated off from the organic phase according to the method according to claim 1.

14. A method for producing isopulegol of the formula (IV)

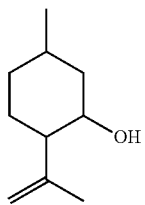
(IV)

comprising

α) the cyclization of citronellal of the formula (V)

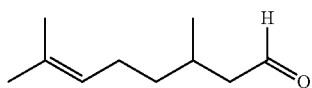
(V)

in the presence of a catalyst which is obtainable by reacting a bis(diarylphenol) ligand of the formula (I) as defined in claim 9,
with an aluminum compound of the formula (II),

(II)

where

Al is aluminum, $R^{14}$ is a branched or unbranched alkyl radical having 1 to 5 carbon atoms and p is 0 or an integer from 1 to 3, and/or with an aluminum compound of the formula (III),

(III)

where

Al is aluminum and

M is lithium, sodium or potassium,

β) the recovery of the bis(diarylphenol) ligand of the formula (I) after the reaction has taken place by
a) subjecting the reaction product obtained in step α) to distillative separation to obtain an isopulegol-enriched top product and an isopulegol-depleted bottom product,
b) bringing the isopulegol-depleted bottom product into close contact with an aqueous base to give an aluminum-containing aqueous phase and an organic phase comprising the majority of the ligands of the formula (I) and
c) separating off the ligand of the formula (I) from the organic phase according to the method according to claim 1.

15. A method for producing menthol comprising the steps:

A) production of isopulegol of the formula (IV) according to claim 14 and
B) hydrogenation of the ethylenic double bond of the isopulegol obtained in this way.

\* \* \* \* \*